(12) United States Patent
Rodriguez Medina et al.

(10) Patent No.: US 8,716,441 B2
(45) Date of Patent: May 6, 2014

(54) UBIQUITIN BINDING POLYPEPTIDES

(75) Inventors: Manuel Salvador Rodriguez Medina, Derio-Vizcaya (ES); Roland Hjerpe, Derio-Vizcaya (ES)

(73) Assignee: Centro de Investigation Cooperativa en Biociencias—CIC BIOGUNE (ES)

( * ) Notice: Subject to any disclaimer, the term of this patent is extended or adjusted under 35 U.S.C. 154(b) by 613 days.

(21) Appl. No.: 12/389,660

(22) Filed: Feb. 20, 2009

(65) Prior Publication Data

US 2009/0220470 A1 Sep. 3, 2009

(30) Foreign Application Priority Data

Feb. 28, 2008 (EP) .................................... 08380059

(51) Int. Cl.
C07K 1/22 (2006.01)
C07K 14/435 (2006.01)
C12N 1/21 (2006.01)
A61K 38/16 (2006.01)

(52) U.S. Cl.
USPC ....... 530/350; 530/300; 424/93.21; 435/69.1; 435/69.7; 435/7.1; 536/23.4

(58) Field of Classification Search
USPC ............... 424/93.21; 530/300, 350; 435/69.1, 435/69.7, 7.1; 536/23.4
See application file for complete search history.

(56) References Cited

U.S. PATENT DOCUMENTS

2003/0215918 A1* 11/2003 Davis et al. .................. 435/69.1

FOREIGN PATENT DOCUMENTS

WO WO03049602 A2 6/2003
WO WO2004106514 9/2004

OTHER PUBLICATIONS

Cavey, J.R., et al., Strategies for the purification of ubiquitylated proteins in frontotemporal dementia, www.biochemistry.org/meetings/abstracts/BS2006/BS20060356.
Gwizdek, C., et al., Ubiquitin-associated domain of Mex67 synchronizes recruitment of the mRNA export machinery with transcription, Proc. Natl. Acad. Sci USA, 2006; 103:16376-81.
Hurley, J., et al., Ubiquitin-binding domains, Biochem J (2006) 399: 361-372, Great Britain.
Layfield, R., et al., Purification of poly-ubiquitinated proteins by S5a-affinity chromatography, Proteomics, 2001; 1:773-7, Wiley-VCH.
Mayor, T., et al., Two-Step Affinity Purification of Multiubiquitylated Proteins from *Saccharomyces cerevisiae*, Methods in Enzymology, 2005; 399:385-92.
Peng, J., et al., Proteomic Analysis of Ubiquitin Conjugates in Yeast, Methods in Enzymology, 2005; 399:367-81, Elsevier Inc.
Hierpe, R., et al., Development of TUBE's (Tandem Ubiquitin Binding Entities) to study ubiquitin processes, (2008), 3rd Proteolysis meeting, Spain.
International Search Report for EP 08 38 0059, (2008).

\* cited by examiner

*Primary Examiner* — Chih-Min Kam
(74) *Attorney, Agent, or Firm* — Caesar, Rivise, Bernstein, Cohen & Pokotilow, Ltd.

(57) ABSTRACT

The invention relates to Tandem Ubiquitin Affinity Entities (TUBES) which are fusion polypeptides comprising at least two ubiquitin binding domains connected to each other by non-naturally occurring spacer regions. The TUBES are capable of binding with high affinity to ubiquitin and to ubiquitylated polypeptides and are therefore suitable for the purification of ubiquitylated polypeptides from cellular extracts as well as for the identification of new ubiquitylated polypeptides.

36 Claims, 26 Drawing Sheets

P62 GST-UBAx1

P62 GST-UBAx4

Fig. 5A
Fig. 5B
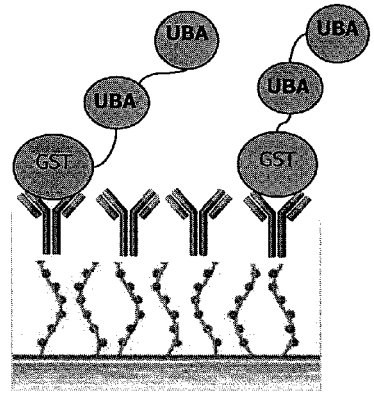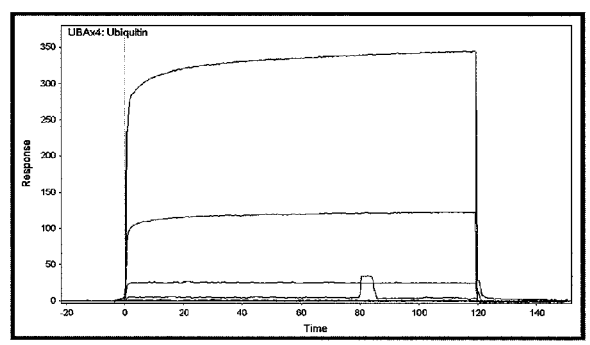
Fig. 5C
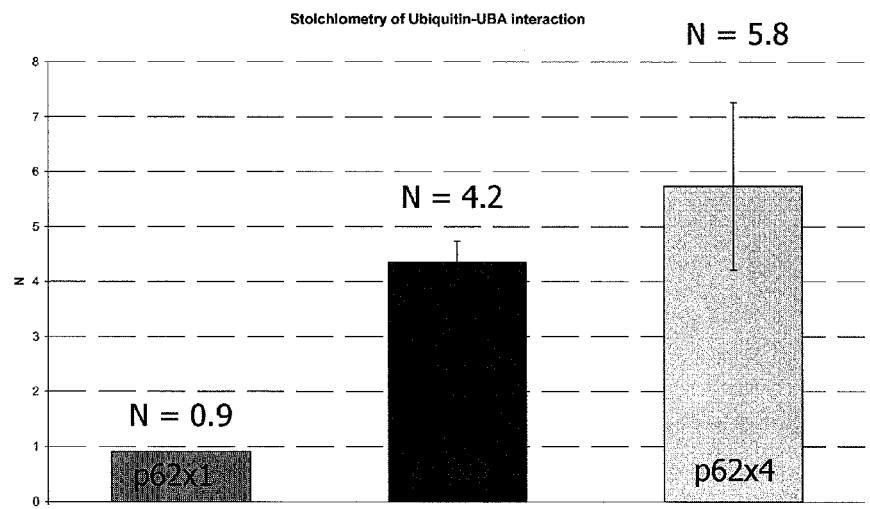

US 8,716,441 B2

UBIQUITIN BINDING POLYPEPTIDES

FIELD OF THE INVENTION

The invention relates to the field of purification of target proteins based on their affinity towards specific binding reagents. In particular, the invention relates to methods for the purification by affinity binding of ubiquitin and ubiquitin-conjugated proteins by the use of fusion proteins comprising tandem arrangements of ubiquitin binding domains derived from naturally occurring ubiquitin-binding proteins.

BACKGROUND OF THE INVENTION

Multiple post-translational modifications contribute to regulate the activity of many essential cellular factors. These modifications yield a quick cellular response to change the activity of the target proteins by modifying among others, their capacity to associate with multiple partners, connect with downstream factors, alter their sub-cellular localisation or promote variations in protein synthesis and degradation. Amongst the different strategies to control protein activity, probably the most drastic one is protein degradation, because it inactivates all protein functions. In eukaryotic cells, the ubiquitin-proteasome system (UPS) drives one of the most important proteolytic activities.

As its name implies, ubiquitin is a ubiquitous and highly conserved protein found in all eukaryotic tissues. The ubiquitin molecule can be found free or conjugated to protein substrates, where it modifies the biochemical properties of the target protein drastically. The attachment of ubiquitin to a protein-substrate is achieved by a cascade of thiol-ester reactions, mediated by an ubiquitin activating enzyme (E1), an ubiquitin conjugating enzyme (E2) and an ubiquitin ligase (E3) as it is shown schematically in FIG. 1.

Ubiquitylation (or ubiquitination) is defined as the process whereby a lysine residue in a substrate molecule is covalently bonded to ubiquitin. Modification of the substrate may be in the form of mono-ubiquitylation (possibly at multiple sites—this is referred to as multiple monoubiquitylation) or as poly-ubiquitylation. Depending on the number of ubiquitin molecules attached to the protein substrate and the lysine residues on the ubiquitin moieties involved in the formation of ubiquitin chains, the destiny of a protein will be different.

To recognise various forms of ubiquitylated targets a limited number of protein effectors will specifically interact with such modified proteins working as "ubiquitin receptors". Such receptor/effector proteins will directly mediate or connect with a function depending on the particular modification and/or modified protein. The property of ubiquitin binding is most often localized to a modular domain, which independently can recognize and interact with ubiquitin.

Ubiquitin binding domains (UBDs) are a diverse family of structurally related dissimilar protein modules which bind mono- and poly-ubiquitin. The first protein motif characterized to bind ubiquitin non-covalently was found in the proteasomal subunit S5a (rpn10 in yeast). S5a is a part of the 19S proteasome regulatory particle, where it links the base to the lid. The ubiquitin binding property of S5a pertains to two independent Ubiquitin Interacting Motifs (UIMs), which are short α helical regions. Following the discovery of the UIM, many other ubiquitin binding domains (UBDs) were characterized, and today at least 16 different motifs have been described, among them the UBA (Ubiquitin Associated domain), UIM (Ubiquitin Interacting Motif), MIU (Motif Interacting with Ubiquitin) domain, DUIM (double-sided ubiquitin-interacting motif), CUE (coupling of ubiquitin conjugation to ER degradation) domain, NZF (Np14 zinc finger), A20 ZnF (zinc finger), UBP ZnF (ubiquitin-specific processing protease zinc finger), UBZ (ubiquitin-binding zinc finger), UEV (ubiquitin-conjugating enzyme E2 variant), PFU (PLAA family ubiquitin binding), GLUE (GRAM-like ubiquitin binding in EAP45), GAT (Golgi-localized, Gamma-ear-containing, Arf (ADP-ribosylation-factor) binding), Jab/MPN (Jun kinase activation domain binding/Mpr1p and Pad1p N-termini), UBM (Ubiquitin binding motif) and a Ubc (ubiquitin-conjugating enzyme). Most UBDs are 20-40 amino acids long structural motifs without sequence conservation that are found in all eukaryotes. Amongst these motifs, the UIM and the UBA domain are the two best characterized.

An important question concerning the trafficking and presentation of modified proteins to the proteasome is how these processes are regulated. Understanding how modified substrates are brought to the proteasome for subsequent degradation may result in the identification of new points of possible therapeutic intervention.

One of the best described UBDs is the UBA domain. The UBA domain family exhibits poor sequence homology, but are structurally well conserved as compact three helix bundles. UBA domains are classified into four different groups, depending on their ubiquitin binding properties. Class 1 and 2 are defined as binding K48 and K63 poly-ubiquitin chains, respectively, class 3 does not bind poly-ubiquitin chains, and class 4 does not exhibit any particular specificity for chain linkage in poly-ubiquitin, whilst binding equally strongly to monoubiquitin. The physiological purpose of the UBA domain will necessarily depend on the nature of the protein which it is found in—however, several UBA domain containing proteins have been suggested to serve as factors shuttling ubiquitylated substrates to the proteasome (e.g. hHR23A, p62, Dsk2). This particular function would be achieved by binding to ubiquitylated substrates through the UBA domain, and binding to the proteasome via another domain, usually an Ubiquitin Like domain (UBL). These domains share homology with ubiquitin, and many have been shown to interact with the proteasome through S5a. In addition to S5a, all other helical UBDs have also been reported to interact with ubiquitin through its hydrophobic surface patch. Hhr23A and Hhr23B (human homologs of yeast proteins Rad23A/B) are examples of UBA/UBL proteins, containing an N-terminal UBL domain and two UBA domains. The function of Hhr23A may be regulated by competition/cooperation arising from intramolecular or intermolecular interactions between its UBAs and UBL. Intramolecular UBL-UBA binding has been suggested to result in a closed domain organization, which may be opened up by binding of S5a UIMs to the Hhr23A UBL, disrupting Hhr23A intramolecular contacts.

There are several documents in the state of the art which describe methods for the isolation and purification of ubiquitylated proteins. For example, document WO04106514 describes a method of recovering protein having been ubiquitylated, comprising recovering ubiquitylated protein with the use of a specific antibody capable of recognizing ubiquitin chains through immunological means, such as affinity chromatography or immunoprecipitation. However, ubiquitin antibodies are expensive and do not show the protective effect reported for some UBA domains which may contribute to increase the efficiency of purification (Gwizdek C, et al. Proc. Natl. Acad. Sci USA., 2006, 103:16376-81). Cavey et al. (Cavey, Jr. et al. www.biochemistry.org/meetings/abstracts/BS2006/BS20060356) have described a method for the purification of ubiquitylated proteins using the UBA domain from p62 protein followed by elution of ubiquitylated proteins.

Such method presents a low affinity-purification of ubiquitylated proteins since a single UBA domain is employed for such purification. Mayor and Deshaies (Methods Enzymol. 2005; 399:385-92) have described an affinity purification protocol using a budding yeast strain expressing hexahistidine-tagged ubiquitin. Such method is a two-step purification method that uses a cell expressing hexahistidine-tagged ubiquitin, thus needing a first modification of the ubiquitin protein and moreover, using of a two-step purification protocol. Peng J. and Cheng D. (Methods Enzymol. 2005; 399: 367-81) have also described a purification protocol for the purification of ubiquitylated proteins in which the ubiquitin protein is modified by adding a His-tag at its N-terminal end thus, needing a first modification of the ubiquitin protein. Layfield et al (Proteomics. 2001, 1:773-7) have described an immobilised glutathione-S-transferase (GST)-S5a fusion protein to purify poly-ubiquitylated proteins from mammalian tissues. Such a proteasomal fusion protein may be mostly suitable for purification of proteins containing Lys48-linked ubiquitin chains. WO03/049602 describes methods for establishing a protein expression profile of a biological sample. Such method comprises purification of ubiquitylated proteins by means of using the UBA domains of an ubiquitin binding protein, such as Rad23, said UBA domains being assembled as multimeric forms of UBA affinity matrices. Thus, said method only describes the use of UBA domains in said multimeric proteins, and moreover, said multiple domains as described therein include no more than two of such UBA domains. On the other hand, BIOMOL commercialises a kit for the isolation and enrichment of ubiquitylated proteins through use of a high-binding affinity matrix. Said matrix comprises single UBDs (ubiquitin binding entities) for binding to ubiquitylated proteins.

Thus, there is a need for the development of a new reliable method for the isolation and purification of ubiquitylated proteins with high affinity for such proteins and which would facilitate further analysis of said isolated protein. Such tools should allow capturing said modified proteins in vitro and/or in living cells.

SUMMARY OF THE INVENTION

The inventors have developed a novel strategy that uses a polypeptide comprising at least two ubiquitin binding domains, wherein said ubiquitin binding domains are linked to each other via a non-naturally occurring intervening amino acid sequence, in order to increase the affinity of these domains for ubiquitylated proteins and facilitates further analysis. These polypeptides can be used in vitro as a solid support for purification of ubiquitylated proteins or as ubiquitin traps to capture modified proteins in living cells. These polypeptides are hereinafter referred to Tandem Ubiquitin Affinity Entities (TUBES).

Thus, in a first aspect, the present invention refers to a polypeptide (hereinafter, the polypeptide of the invention) comprising at least two ubiquitin binding domains, wherein said ubiquitin binding domains are linked to each other via a non-naturally occurring intervening amino acid sequence.

In a second aspect, the invention refers to a method for real time protein interaction analysis in vivo which comprises
 (i) introducing into a cell a first gene construct encoding a protein comprising a polypeptide of the invention, a first member of a binding pair and a detectable tag and a second gene construct encoding a protein comprising a ubiquitylation signal and a detectable tag into a cell,
 (ii) maintaining the cells under conditions allowing the expression of said gene constructs and allowing the interaction between the UBD of the protein encoded by the first gene construct and the ubiquitin added to the ubiquitylation signal of the protein encoded by the second construct and
 (iii) measuring the interaction of both proteins using the detectable tags.

In a third aspect, the invention refers to a Method for real time protein interaction analysis in vitro which comprises,
 (i) immobilizing in a surface a polypeptide according of the invention,
 (ii) contacting said immobilized polypeptide with an ubiquitylated protein which comprises a detectable tag in conditions allowing the interaction between the UBD of the first protein and the ubiquitin molecules of the second protein, and
 (iii) measuring of the interaction of the both proteins.

In a further aspect, the invention refers to a nucleotide sequence encoding a polypeptide according to the invention.

In a further aspect, the invention refers to a gene construct comprising a nucleotide sequence according to the invention.

In another aspect, the invention refers to an expression vector comprising a nucleotide sequence or a gene construct according to the invention.

In another aspect, the present invention refers to a cell comprising a nucleotide sequence, or a gene construct, or a vector according to the invention.

In a further aspect, the invention also refers to a non-human animal comprising a nucleotide sequence, or a gene construct, or a vector, or a cell according to the present invention.

In another aspect, the invention refers to a process for obtaining a polypeptide according the invention, which comprises culturing a cell according to the present invention under conditions which allow producing said polypeptide and, if desired, recovering said polypeptide from the culture medium.

In a further aspect, the invention refers to an in vitro method for the isolation of a ubiquitylated protein from a sample which comprises
 i) incubating a polypeptide of the invention with said sample in conditions allowing said polypeptide to interact with said ubiquitylated protein present in said sample; and
 ii) recovering said ubiquitylated protein which is bound to said polypeptide.

In another aspect, the invention refers to an in vitro method for the isolation of a protein comprising a ubiquitylation signal which comprises
 i) introducing a first gene construct encoding a protein comprising at least a UBD and a first member of a binding pair and a second gene construct encoding a protein comprising a ubiquitylation signal into a cell in conditions allowing the expression of said gene constructs in and in conditions allowing the interaction between the UBD of the protein encoded by the first gene construct and the ubiquitin added to the ubiquitylation signal of the protein encoded by the second construct;
 ii) lysing the cells and
 iii) recovering said protein complex from the lysate obtained in step (ii) using a second member of the binding pair.

In another aspect, the invention refers to a kit comprising a polypeptide according to the invention.

In another aspect, the invention refers to a method for the treatment of a deubiquitylation related disorder which comprises the administration to a subject in need there of the polypeptides of the invention.

In a last aspect, the invention refers to a method for the treatment of a disease caused by a deregulation of the proteasome degradation of at least one ubiquitylated polypeptide which comprises the administration to a subject in need thereof of the polypeptides of the invention.

BRIEF DESCRIPTION OF THE FIGURES

(FIG. 4B) Purified TUBEs can readily be detected by anti-GST, anti-His6 and anti-SV5 antibodies. (FIG. 4C) Mono-ubiquitin interaction with single and tandem UBA domains from hHR23A and ubiquilin1 was monitored by real-time surface plasmon resonance (SPR). UBAs or TUBEs were captured on a Biacore chip surface through their GST moiety, to a level of 150-220 resonance units (RU). A 2-fold series of dilutions of ubiquitin (60 nM-1.5 μW was then injected in a randomized order (insets). The measured SPR signals were plotted against the ubiquitin concentration, to determine the affinity constants (Kd) and binding stoichiometries (n), and their respective standard deviations.

FIGS. 5A through 5C. Analysis of molecular interactions between the polypeptide of the invention comprising the UBD of p62 and ubiquitin by Surface Plasmon Resonance (BIACORE). Top panel left (FIG. 5A) illustrates the attachment and orientation of the polypeptide on the sensor chip. Top right panel (FIG. 5B) shows real time interactions of different concentrations of ubiquitin to said polypeptide expressing four copies of the UBA domain of p62. Lower panel (FIG. 5C) illustrate fold of ubiquitin binding to one, three or four UBAs of p62.

(FIGS. 6A, 6B, 6C, 6D) SPR monitoring of the interaction of K48 and K63 tetra-ubiquitin with hHR23A and ubiquilin1 TUBEs, as indicated. TUBEs were captured to a density of 30 RU, over which 2-fold series of dilutions of K48 tetra-ubiquitin (1.25-80 nM) or K63 tetra-ubiquitin (0.11-30 nM) were injected (insets). The measured steady-state SPR signals were plotted against the tetra-ubiquitin concentration, to determine the affinity constants (Kd) and binding stoichiometries (n), and their respective standard deviations. (FIG. 6E) No interaction can be detected between single UBAs and tetra-ubiquitin, up to concentrations of 80 nM (K48 tetra-ubiquitin) and 40 nM (K63 tetra-ubiquitin). (FIG. 6F) Cartoon illustrating some of the potential binding modes of tetra-ubiquitin to TUBEs. U=ubiquitin. TUBEs=clipped grey circles.

FIG. 7A shows the principle used to purify ubiquitylated proteins using the method of the invention. FIG. 7B shows results obtained from a typical experiment after recovery of bound and unbound fractions to the polypeptide of the invention comprising the UBD of p62. FIGS. 7C and 7D show the results obtained from experiments using the UBDs of hHR23A (UBA1) and Ubiquilin1. Western blot detection was performed with the indicated antibodies.

FIG. 8A shows sensorgrams representing a concentration series of one only p62-UBA (p62×1) domain GST fusion injected over the chip surface. FIG. 8B shows sensorgrams representing a concentration series of four domains of the p62-UBA (p62×4) fused to GST injected over the chip surface. A markedly slower dissociation rate of p62×4 from the K63 tetra ubiquitin can be observed. Further, a higher maximum signal intensity can be observed for p62×4, suggesting a more efficient binding respective to p62×1. Similar results have been observed concerning the ubiquilin1 UBA domain.

(FIG. 9A) Schematic representation of the traditional GST pull-down method, using DUB inhibitors IAA and NEM. (FIG. 9B) Schematic representation of the modified pull-down method in the presence of TUBEs and absence of IAA/NEM. TUBEs (clipped grey circles) are allowed to form complexes with poly-ubiquity-lated proteins during lysis, and intact complexes are then pulled down using glutathione agarose beads. (FIG. 9C) Western blot analysis of cell lysates prepared according to scheme (FIG. 9A) in the presence of IAA and NEM: detection using either Ponceau staining, or anti-IκBα, anti-poly-ubiquitin, or anti-SV5 antibodies. (FIG. 9D) Western blot analysis of cell lysates prepared according to scheme (FIG. 9B) in the presence of TUBEs: detection using either Ponceau staining, or anti-IκBα, anti-poly ubiquitin, or anti-SV5 antibodies. Asterisk-IκBα (the same membrane was used for SV5 and IκBα detection)

(FIG. 10A) Evaluation of ubiquitin de-conjugation in cell extracts, in the presence of purified TUBEs (3 μM), UBAs (4.4 μM) or IAA/NEM (10 mM) was monitored by Western blot analysis with anti-poly-ubiquitin and anti-SV5 antibodies. Cell extracts incubation in lysis buffer or lysis buffer supplemented with GST were included as controls. Anti-Sam68 and Ponceau staining (total protein) are included as charge controls. (FIG. 10B) Evaluation of the protective effect over time of IAA/NEM (10 mM) or TUBEs (7.2 μM). Anti-Sam68 and Ponceau staining are included as charge controls. (FIG. 10C and FIG. 10D) TUBEs protective capacity was unaffected after 16 hours of incubation with cell lysates and was detectable even when TUBEs were used at concentrations as low as 0.17 μM (1 μg/100 μl of lysate). (FIGS. 10E and 10F, respectively) In vitro transcribed-translated p53 was subjected to proteasomal degradation using either reticulocyte extract (RE) or purified proteasomes (PP).

(FIG. 11A) WT p53 MCF-7 breast cancer cells were pulsed with doxorubicin (10

µM), after which cells were replenished with fresh DMEM. Cells were then harvested at the indicated times, and Western blot analysis was performed to detect p53 or MDM2. Sam68 was detected as a control of charge. (FIG. 11B) WT p53 MCF-7 cells were treated as in (FIG. 11A), and subjected to pull-down using 40 µg (7.2 µM) of the two different TUBEs and glutathione agarose beads. Western blot analysis was performed with anti-pS3, anti-Mdm2 and anti-SV5 antibodies. (FIG. 11C) WT p53 MCF-7 cells were treated as in (11A) (3 h post pulse). Ubiquitylated proteins were purified using TUBE hHR23A, anti-ubiquitin antibodies FK1 and P4D1 or nickel beads. His$_6$-ubiquitin purification was performed under denaturing conditions. SV5-IP was used as control. Western blot analysis was performed with the indicated antibodies.

DETAILED DESCRIPTION OF THE INVENTION

Figure 1:
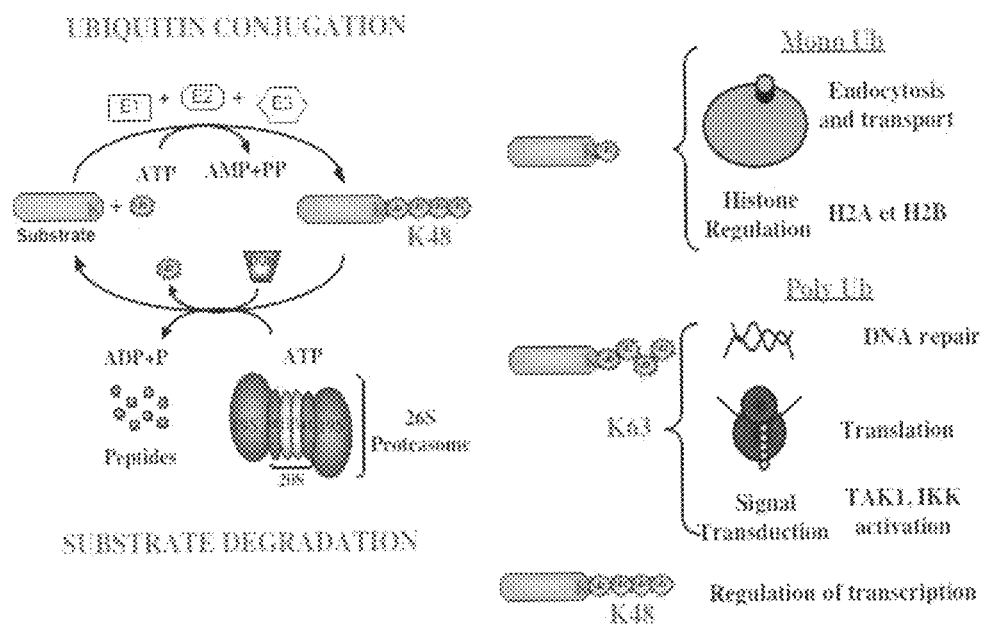
FIG. 1. The Ubiquitin-proteasome pathway (UPS). Ubiquitin is covalently attached to protein targets through a thiol-ester cascade mediated by the E1, an E2 and a specific E3. The functional consequences of such modification could be very diverse depending on the internal lysine residue used to form ubiquitin-chains. Some examples are illustrated in this figure.

The inventors of the present invention have developed a new effective tool for the isolation of ubiquitylated proteins by means of generating polypeptides comprising multiple ubiquitin affinity domains. The inventors have engineered polypeptides comprising at least two ubiquitin binding domains which show an increased affinity for individual ubiquitin binding domains present in ubiquitin-modified targets and allowing the study of post-modification mechanisms, connecting signalling cascades with effectors functions. Moreover, the constructs comprising multiple ubiquitin binding domains show a slower dissociation from polyubiqutin targets and, in particular, from tetraubiquitin.

Polypeptides of the Invention

Thus, in a first aspect, the invention refers to a polypeptide, hereinafter polypeptide of the invention, comprising at least two ubiquitin binding domains, wherein said ubiquitin binding domains are linked to each other via a non-naturally occurring intervening amino acid sequence.

Protein domains can be defined as segmented portions of a polypeptide sequence that assume stable three-dimensional structures. The term "ubiquitin binding domain" as used herein, refers to a protein domain, which independently can recognize and interact with ubiquitin. Most ubiquitin binding domains known in the state of the art are 20-40 amino acids long structural motifs and are found in all eukaryotes. In a particular embodiment of the invention, said ubiquitin binding domain is selected from the group consisting of an UBA (Ubiquitin Associated domain), UIM (Ubiquitin Interacting Motif), MIU (Motif Interacting with Ubiquitin) domain, DUIM (double-sided ubiquitin-interacting motif), CUE (coupling of ubiquitin conjugation to ER degradation) domain, NZF (Np14 zinc finger), A20 ZnF (zinc finger), UBP ZnF (ubiquitin-specific processing protease zinc finger), UBZ (ubiquitin-binding zinc finger), UEV (ubiquitin-conjugating enzyme E2 variant), PFU (PLAA family ubiquitin binding), GLUE (GRAM-like ubiquitin binding in EAP45), GAT (Golgi-localized, Gamma-ear-containing, Arf-binding), Jab/MPN (Jun kinase activation domain binding/Mpr1p and Pad1p N-termini), UBM (Ubiquitin binding motif) and a Ubc (ubiquitin-conjugating enzyme).

According to the invention, the ubiquitin binding domains comprised in the polypeptide of the invention can be equal or different.

As mentioned above, the polypeptide of the invention comprises at least two ubiquitin binding domains which are linked to each other via a non-naturally occurring intervening amino acid sequence. According to the invention, said non-naturally occurring intervening amino acid sequence act as a hinge region between said domains, allowing them to move independently of one another while maintaining the three-dimensional shape of the individual domains. In that sense, a preferred non-naturally occurring intervening amino acid sequence according to the invention would be a hinge region characterized by a structural softness that enables this motion. In a particular embodiment, said non-naturally occurring intervening sequence is a non-naturally occurring flexible linker. In a preferred embodiment, said flexible linker is a flexible peptide linker with a length of 20 or less amino acids. In a more preferred embodiment, the peptide linker comprises 2 or more amino acids selected from the group consisting of glycine, serine, alanine and threonine. In a preferred embodiment of the invention, said flexible linker is a poly-glycine linker. Possible examples of flexible linker/spacer sequences include SGGTSGSTSGTGST (SEQ ID NO: 28), AGSSTGSSTGPGSTT (SEQ ID NO: 29) or GGSGGAP (SEQ ID NO: 30). These sequences have been used for the linking of designed coiled coils to other protein domains (Muller, K. M., Arndt, K. M. and Alber, T., Meth. Enzymology, 2000, 328:261-281). Preferably, said linker comprises or consist of the amino acid sequence GGGVEGGG (SEQ ID NO: 11).

The effect of the linker region is to provide space between the UBDs. Thereby it is ensured that the secondary structure of the UBDs is not affected by the presence of the neighbouring UBDs so that the function of the UBDs is maintained. Preferably, the spacer is of polypeptide nature. In this way the nucleic acid sequence encoding the spacer can be inserted between the sequences encoding the UBDs and the whole construct can be produced at the same time. The linker peptide preferably comprises at least two amino acids, such as at least three amino acids, for example at least five amino acids, such as at least ten amino acids, for example at least 15 amino acids, such as at least 20 amino acids, for example at least 30 amino acids, such as at least 40 amino acids, for example at least 50 amino acids, such as at least 60 amino acids, for example at least 70 amino acids, such as at least 80 amino acids, such as at least 90 amino acids such as approximately 100 amino acids.

The linker may be linked to the flanking UBD components through covalent linkages and preferably the spacer is essentially non-immunogenic, and/or is not prone to proteolytic cleavage, and/or does not comprise any cysteine residues. Similarly, the three-dimensional structure of the spacer is preferably linear or substantially linear. The following are examples of spacer sequences, which are believed to be especially preferable for linking UBDs.

Preferred examples of spacer or linker peptides include those which have been used to link proteins without substantially impairing the function of the linked proteins or at least without substantially impairing the function of one of the linked proteins. More preferably the linkers or spacers have been used to link proteins comprising coiled-coil structures.

The linker may include the tetranectin residues 53-56, which in tetranectin forms a -β-strand, and the residues 57-59 which forms a turn in tetranectin (Nielsen B B et al., FEBS Lett. 412:388-396, 1997). The sequence of the segment is GTKVHMK (SEQ ID NO: 31). This linker has the advantage that when present in the native tetranectin, it is bridging the trimerisation domain with the CRD-domain, and hence is imagined to be well suited for connecting the trimerisation domain to another domain in general. Furthermore the resulting construct is not expected to be more immunogenic than the construct without a linker.

Alternatively, the linker may be chosen as a sub-sequence from the connecting strand 3 from human fibronectin, this corresponds to amino acid residues 1992-2102 (SWIS-SPROT numbering, entry P02751). Preferably the subsequence: PGTSGQQPSVGQQ (SEQ ID NO: 32) covering amino acid residues number 2037-2049 is used, and within that subsequence the segment GTSGQ (SEQ ID NO: 33) corresponding to amino acid residues 2038-2042 is more preferable. This construct has the advantage that it is know not to be highly prone to proteolytic cleavage and is not expected to be highly immunogenic bearing in mind that fibronectin is present at high concentrations in plasma.

Alternatively, a suitable linker peptide may be based in the 10 amino acid residue sequence derived from the upper hinge region of murine IgG3. This peptide (PKPSTPPGSS) (SEQ ID NO: 34) has been used for the production of antibodies dimerised trough a coiled coil (Pack P. and Pluckthun, A. Biochemistry 31, pp 1579-1584 (1992)) and may be useful as a spacer peptide according to the present invention. Even more preferable may be a corresponding sequence from the upper hinge region of human IgG3. Sequences from human IgG3 are not expected to be immunogenic in human beings.

In a particular embodiment of the invention, the polypeptide of the invention further comprises the amino acid sequence of a tag. Said tag includes but is not limited to: polyhistidine tags (His-tags) (for example H6 and H10, etc.) or other tags for use in IMAC systems, for example, Ni2+ affinity columns, etc., GST fusions, MBP fusions, streptavidine-tags, the BSP biotinylation target sequence of the bacterial enzyme BIRA and tag epitopes that are directed by antibodies (for example c-myc tags, FLAG-tags, among others). As will be observed by a person skilled in the art, said tag peptide can be used for purification, inspection, selection and/or visualization of the fusion protein of the invention. In a particular embodiment of the invention, said tag is a detection tag and/or a purification tag. Inventors have shown (see Example) that when the polypeptide of the invention comprises an N-terminal His6x tag and a C-terminal epitope, these can be recognised by specific antibodies allowing immunoprecipitation, immunodetection (ELISA and Western-blot) and sub-cellular distribution by indirect immunofluorescence. Hence, in a preferred embodiment of the invention, said detection tag is the Sv5 epitope tag and said purification tag is a polyhistidine tag.

Inventors have surprisingly observed that the polypeptides of the invention show an increased affinity for ubiquitin or ubiquitylated proteins when said polypeptides contain more than one ubiquitin binding domains. Indeed, using surface plasmon resonance technology (see FIGS. 5A through 5C and 8A through 8B), the inventors tested the capacity of the polypeptides of the invention to interact with ubiquitin. The results indicate that the capacity of interaction increased with the number of ubiquitin binding domains copies expressed, being said interaction capacity increased in four and six times when two and four copies of said ubiquitin binding domains were present, respectively.

Thus, in a particular embodiment of the invention, the polypeptide of the invention comprises at least four ubiquitin binding domains. In a more particular embodiment, said ubiquitin binding domains are UBA domains. In a yet more particular embodiment, said UBA domains are the UBA domains from HR23A, p62 and/or ubiquilin 1 proteins.

In a more particular embodiment of the invention, said HR23A UBA domains are the UBA domains 1 and/or 2 from the hHR23A protein (SEQ ID NO: 12 and SEQ ID NO: 13, respectively) and/or functionally equivalent variants thereof. In a preferred embodiment, said polypeptide comprises four HR23A UBA1 domains and/or functionally equivalent variants thereof and in another preferred embodiment, said polypeptide comprises four HR23A UBA2 domains and/or functionally equivalent variants thereof. In a more particular embodiment of the invention, said polypeptide is selected from the group consisting of SEQ ID NO: 1 and SEQ ID NO: 2.

In another particular embodiment, said UBA domains are the UBA domains from p62 (SEQ ID NO: 14) and/or ubiquilin-1 (SEQ ID NO: 15) proteins. In a preferred embodiment, said polypeptide comprises four p62 UBA domains and/or functionally equivalent variants thereof. In another preferred embodiment, said polypeptide comprises four ubiquilin-1 UBA domains and/or functionally equivalent variants thereof. In a more preferred embodiment, said polypeptide is selected from the group consisting of SEQ ID NO: 3 and SEQ ID NO: 4.

In another particular embodiment of the invention, said ubiquitin binding domain is an UIM domain. In a more particular embodiment, said UIM domain is an UIM domain from the S5a protein and/or functionally equivalent variants thereof. In a yet more particular embodiment, said polypeptide comprises eight UIM domains and/or functionally equivalent variants thereof. In an even more particular embodiment, said polypeptide comprises four S5a UIM-1 (SEQ ID NO: 16) domains and four S5a UIM-2 (SEQ ID NO: 17) domains and/or functionally equivalent variants thereof. In a preferred embodiment, said polypeptide comprises the amino acid sequence disclosed in SEQ ID NO: 5.

A person of ordinary skill in the art will recognize that the present invention relates not only to the specific amino acid sequences disclosed in the specification, but also to variants thereof, specifically to functionally equivalent variants thereof, such as fragments, analogues and/or derivatives. Thus, a variant of a specific amino acid sequence preferably retains at least one biological function or activity of the specific amino acid sequence, preferable the ability to bind to ubiquitin or to an ubiquitylated protein.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNA$_{LYS}$), could be modified with an amine specific photoaffinity label.

The term "functionally equivalent" as used herein refers to a polypeptide according to the invention that preferably retains at least one biological function or activity of the specific amino acid sequence of a UBD domain, preferable the ability to bind to ubiquitin or to an ubiquitylated protein. An illustrative, non limitative, way of testing the capacity of such variants of the polypeptide of the invention to interact with ubiquitin or a ubiquitylated protein is by means of using Surface Plasmon Resonance (SPR) technology (see Example 1 and FIGS. 5A through 5C and 8A through 8B).

As explained before, the polypeptides of the invention can be fused to another polypeptide or tag, such as a leader or secretory sequence or a sequence which is employed for purification or for detection. In a particular embodiment, the polypeptide of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, said glutathione modified support is a glutathione-agarose bead. Additionally, a sequence encoding a protease cleavage site can be included between said affinity tag and the polypeptide sequence, thus permitting the removal of the binding tag after incubation with this specific enzyme and thus facilitating the purification of the corresponding protein of interest. Suitable protease cleavage sites for incorporation into the polypeptides of the invention include enterokinase (cleavage site Asp-Asp-Asp-Asp-Lys) (SEQ ID NO: 35), factor Xa (cleavage site Ile-Glu-Gly-Arg (SEQ ID NO:36) or Ile-Asp-Gly-Arg (SEQ ID NO: 37)), thrombin (cleavage site Leu-Val-Pro-Arg-Gly-Ser) (SEQ ID NO: 38), TEV protease (cleavage site Glu-Asn-Leu-Tyr-Phe-Gln-Gly) (SEQ ID NO: 39), PreScission protease (cleavage site Leu-Glu-Val-Leu-Phe-Gln-Gly-Pro) (SEQ ID NO: 40), inteins and the like.

Figure 3A:
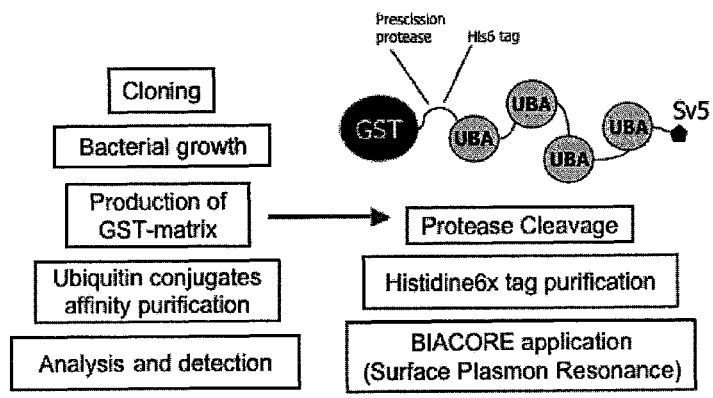
FIGS. 3A through 3D. Strategy for the preparation, purification and detection of polypeptides affinity. Top part illustrates the steps of purification of the polypeptides of the invention to be used as affinity columns or for BIACORE analysis. Middle part illustrates purification steps for said polypeptides containing one or four UBA domains. Lower part illustrates detection of purified proteins with one to four UBA domains detected by Coomassie blue or by Western-blot with anti SV5 or anti-GST antibodies.
Figure 3B:
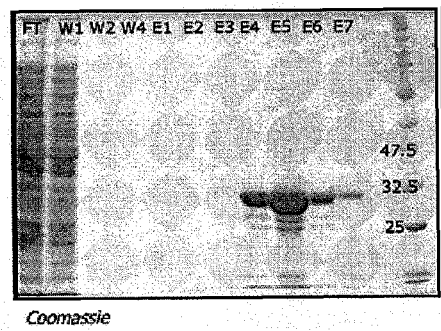
Figure 3C:
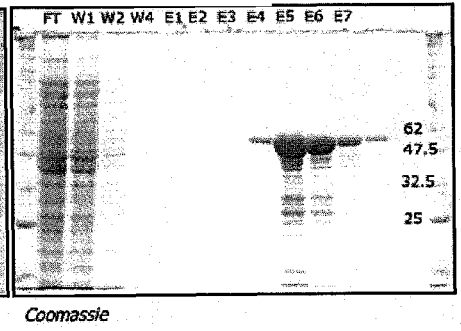
Figure 3D:
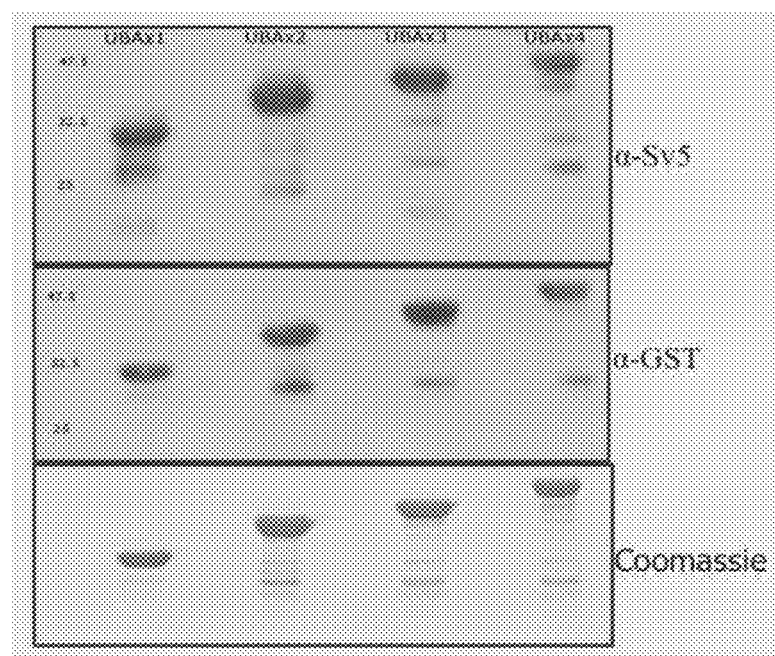

In a particular embodiment, the polypeptide of the invention comprises 4 UBA domains attached through its N-terminus to a GST moiety and through its C-terminus to a detection tag, in particular, the Sv5 tag and comprises, additionally, a protease cleavage site between the GST moiety and the first UBA domain and a polyhistidine tag between the protease cleavage site and the first UBA domain. A schematic representation of such a construct can be seen in FIG. 3A. In preferred embodiments, the fusion polypeptide comprises 2, 3 or 4 UBA domains derived from p62 (see FIG. 3).

As mentioned above, the inventors have shown that the polypeptides of the invention can bind to ubiquitin or ubiquitylated proteins. Thus, in another aspect, the invention refers to the use of the polypeptide of the invention for the isolation of ubiquitylated proteins. In a particular embodiment, the isolation of said ubiquitylated proteins is carried out in vitro and/or ex vivo, for example, as described in the Example 1 accompanying the present invention.

Nucleotide Sequences, Gene Constructs, Expression Vectors and Cells

In another aspect, the invention refers to a nucleotide sequence encoding the polypeptide of the invention. In a particular embodiment, said sequence is selected from the group consisting of SEQ ID NO: 6, SEQ ID NO: 7, SEQ ID NO: 8, SEQ ID NO: 9 and SEQ ID NO: 10.

The nucleotide sequences of the invention can alternatively have sequence variations with respect to the original nucleotide sequences (SEQ ID NO: 6, SEQ ID NO: 7, SEQ ID NO: 8, SEQ ID NO: 9 and SEQ ID NO: 10), for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences of the invention and encodes a polypeptide of the invention.

In the sense used in this description, a nucleotide sequence is "substantially homologous" to any of the nucleotide sequences describe above when its nucleotide sequence has a degree of identity with respect to the nucleotide sequence of the invention of at least 60%, advantageously of at least 70%, preferably of at least 85%, and more preferably of at least 95%. A nucleotide sequence that is substantially homologous to the nucleotide sequence of the invention can typically be isolated from a producer organism of the polypeptide of the invention based on the information contained in said nucleotide sequence, or it is constructed based on the DNA sequence shown in SEQ ID NO: 6, SEQ ID NO: 7, SEQ ID NO: 8, SEQ ID NO: 9 and SEQ ID NO: 10, by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art. The identity between two amino acid sequences is preferably determined by using the BLASTN algorithm [BLAST Manual, Altschul, S., et al., NCBI NLM NIH Bethesda, Md. 20894, Altschul, S., et al., J. Mol. Biol. 215: 403-410 (1990)].

In another aspect, the invention relates to a gene construct, hereinafter gene construct of the invention, comprising said nucleotide sequence of the invention. In a particular embodiment, said gene construct is operatively bound to transcription, and optionally translation, control elements.

The gene construct of the invention can incorporate an operatively bound regulatory sequence of the expression of the nucleotide sequence of the invention, thus forming an expression cassette. As used in this description, the expression "operatively bound" means that the polypeptide of the invention, encoded by the nucleotide sequence of the invention, is expressed in the correct reading frame under the control of expression control or regulatory sequences.

Control sequences are sequences controlling and regulating the transcription and where appropriate, the translation of the polypeptide of the invention, and include promoter sequences, transcriptional regulator-encoding sequences, ribosome-binding sequences (RBS) and/or transcription termination sequences. In a particular embodiment, said expression control sequence is functional in prokaryotic organisms and cells, for example, bacteria, etc., whereas in another particular embodiment, said expression control sequence is functional in eukaryotic organisms and cells, for example, insect cells, plant cells, mammal cells, etc. Examples of well known promoters suitable for carrying out the invention include constitutive promoters such as those found in some eukaryotic viruses (polyoma virus, adenovirus, SV40, CMV, avian sarcoma virus, hepatitis B virus, metalothionein gen promoter, herpes simplex virus thymidine kinase promoter, retroviral LTR regions, immunoglobulin promoter, actin promoter, EF-1alpha promoter as well as inducible promoters wherein expression of the downstream gene requires addition of a substance of an exogenous signal to the culture such as the tetracycline promoter, NFκB/UV light, Cre/lox, heat shock promoters, regulatable RNA polymerase II promoters described in WO/2006/135436 as well as tissue-specific promoters, such as the PSA promoter described in WO2006012221. Advantageously, the construct of the invention further comprises a marker or gene encoding a motif or a phenotype which allows screening the host cell transformed with said construct. In a particular embodiment, the expression of said gene construct is externally controlled. In a more particular embodiment, the expression is externally controlled using the doxycycline Tet-On system.

The gene construct of the invention can be obtained by means of using techniques that are widely known in the state of the art [Sambrook et al., "Molecular cloning, a Laboratory Manual", 2nd ed., Cold Spring Harbor Laboratory Press, N.Y., 1989 Vol 1-3].

The gene construct of the invention can be inserted in a suitable vector. Therefore, in another aspect, the invention relates to a vector, hereinafter vector of the invention, comprising the nucleotide sequence of the invention or the gene construct of the invention. The choice of the vector will depend on the host cell in which it is to be subsequently introduced. In a particular embodiment, the vector of the invention is an expression vector. Vectors suitable for the insertion of said polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

By way of illustration, the vector in which said nucleic acid sequence is introduced can be a plasmid which is or is not integrated in the genome of a host cell when it is introduced in said cell. Illustrative, non-limiting examples of vectors in which the nucleotide sequence of the invention or the gene construct of the invention can be inserted include a tet-on inducible vector for expression in eukaryote cells.

The vector of the invention can be obtained by conventional methods known by persons skilled in the art [Sambrook et al., "Molecular cloning, a Laboratory Manual", 2nd ed., Cold Spring Harbor Laboratory Press, N.Y., 1989 Vol 1-3]. In a particular embodiment, said vector is a vector useful for transforming animal cells.

The vector of the invention can be used to transform, transfect, or infect cells which can be transformed, transfected, or infected by said vector. Said cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example.

Therefore, in another aspect, the invention relates to a host cell, hereinafter cell of the invention, transformed, transfected or infected with a vector provided by this invention.

The cell of the invention therefore comprises a polynucleotide of the invention, a gene construct of the invention, an expression cassette provided by this invention or a vector of the invention, and can express the polypeptide of the invention.

The cell of the invention can be a eukaryotic cell, such as a yeast cell, *S. cerevisiae*, for example, or a prokaryotic cell, such as a bacterium, *E. coli* or *B. subtilis*, for example. Illustrative, non-limiting examples of cells which can be used to obtain cells of the invention include, for example, epithelial kidney 293 cells or U2OS cells.

The cells of the invention can be obtained by conventional methods known by persons skilled in the art [Sambrook et al., 1989, mentioned above].

The described nucleotide sequences, vectors or cells of the invention can be used to obtain a transgenic non-human animal having, inserted in the genome thereof, the nucleotide sequence of the polypeptides of the invention together with the regulatory sequences thereof.

Therefore, in another aspect, the invention relates to a non-human animal, hereinafter non-human animal of the invention, comprising a nucleotide sequence of the invention, or a gene construct of the invention, or a vector of the invention, or a cell of the invention. In a particular embodiment of the invention, the non-human animal of the invention is a mammal, preferably a rodent, more preferably a mouse or a rat. The non-human animal of the invention can have any genetic background of those known in the state of the art by a person skilled in the art.

In another aspect, the invention refers to a process for obtaining a polypeptide of the invention, which comprises culturing a cell of the invention under conditions which allow producing said polypeptide and, if desired, recovering said polypeptide from the culture medium. Conditions for optimizing the culture of said cell will depend on the cell used and are well known to the skilled person in the art. The process for producing the polypeptide of the invention optionally includes isolating and purifying said polypeptide of the invention. The polypeptide of the invention can be purified from the culture medium or from cell extracts (see Example 1). The polypeptide of the invention is conveniently captured using a suitable purification matrix, being, once eluted, concentrated using a commercially available protein concentrating filter, for example, Amicon or Millipore Pellicon, as known in the state of the art.

Methods for the Purification of Ubiquitilyated Proteins

In another aspect, the invention refers to an in vitro method for the isolation of a ubiquitylated protein from a sample which comprises
  i) incubating a polypeptide of the invention with said sample in conditions allowing said polypeptide to interact with said ubiquitylated protein present in said sample; and
  ii) recovering said ubiquitylated protein which is bound to said polypeptide.

In a particular embodiment, the recovering step is carried out by means of using an affinity column. A schematic representation of the method for the isolation of ubiquitylated proteins from cell extracts is depicted in FIG. 5A.

In a particular embodiment, said sample is a cell extract. In a still more preferred embodiment, the cell extract is a tissue extract. As explained in the Examples accompanying the present invention, in order to purify the ubiquitylated proteins from cell extracts, cells are first pre-treated with a proteasome inhibitor. The reason for this is that many ubiquitylated proteins are rapidly turned over by proteasomes, making this transient event difficult to detect. Thus in a preferred embodiment of the invention, when said sample is a cell extract, cells are first pre-treated with a proteasome inhibitor previous to obtain said cell extract. In a particular case, such proteasome inhibitor is MG132 or lactacystin.

An additional factor to consider is the presence of deubiquitylating enzymes (isopeptidases) in the cell extract, which can remove the ubiquitin molecules from the protein of interest, thereby preventing detection of the ubiquitylated species. These problems can be avoided, for example, by preparing the extraction buffer with noxious compounds such as the iodoacetamide or N-Ethylmaleimide (NEM), which blocks the critical cysteine residue present in the active site of most deubiquitylating enzymes. Another important aspect to consider is the conditions under which a protein is ubiquitylated and degraded, being critical to establish the conditions that promote substrate degradation if ubiquitylated forms are to be detected. Another factor to consider is the abundance of the protein of interest. In some cases, the ubiquitylation of an endogenous protein can be assessed, whereas in others, overexpression of the target protein is required. Additionally, it is necessary to denature the extract before purification of the target protein to demonstrate that the protein of interest is itself ubiquitylated and not merely binding to additional co-purified proteins that are ubiquitylated.

The method of the invention can also be used to quantitatively and qualitatively discriminate stimuli-mediated formation of poly-ubiquitin chains on a given protein. As shown in example 7 of the present invention, the polypeptides of the invention can be used to detect oscillations in the amount of p53 in a cell in response to a genotoxic insult. Thus, in a preferred embodiment, the sample is obtained from a cell which has been placed under conditions adequate for promoting ubiquitylation of a given protein.

The condition may be any stimuli which would result in the modification of the levels of ubiquitylated proteins in said cells (see example 7). Examples of these treatments could be the changing of the culture conditions (e.g. hypoxia) or the treatment with a compound that could modify the levels of ubiquitylated proteins in said cells. Moreover, a signal can be used that mimics a situation occurring under disease conditions. The cells that can be used in the present method are the same as described elsewhere in the specification.

After recovering said ubiquitylated protein bound to the polypeptide of the invention, elution of said protein of interest can be carried out by means of, for example, incubation with a specific enzyme, such as a protease, when the polypeptide of the invention comprises a target site for such enzymes, facilitating the purification of the corresponding protein, or by deubiquitylating the recovered ubiquitylated protein using a deubiquitylation enzyme (isopeptidase) as described, for example, in WO0406514, or alternatively, using denaturing conditions.

The presence of an ubiquitylated protein in the cell sample can then be further determined by any analytical means known for characterising proteins, such as detection using specific antibodies, mass spectrometry and characterisation of the spectral peak and the like.

In another aspect, the invention refers to an in vitro method for the isolation of a protein comprising an ubiquitylation signal which comprises
  i) introducing a first gene construct encoding a protein comprising at least a UBD and a first member of a binding pair and a second gene construct encoding a protein comprising a ubiquitylation signal into a cell in conditions allowing the expression of said gene constructs in and in conditions allowing the interaction between the UBD of the protein encoded by the first gene construct and the ubiquitin added to the ubiquitylation signal of the protein encoded by the second construct;
  ii) lysing the cells; and
  iii) recovering said protein complex from the lysate obtained in step (ii) using a second member of the binding pair.

In the first step of the method of the invention, the gene constructs are introduced in the cell. Said step can be carried out using standard procedures for delivering a nucleic acid to the interior of the cell, (see sections 9.1 to 9.5 in Ausubel, F.

M. et al., Current Protocols in Molecular Biology, John Wiley & Sons Inc; ringbou edition, 2003). In particular, the cells can be transfected by means of precipitating DNA with calcium phosphate, DEAE-dextran, polybrene, electroporation, microinjection, liposome-mediated fusion, lipofection, infection by retrovirus and biolistic transfection.

Examples of suitable binding pairs according to the invention include hapten or antigen/antibody, e.g. digoxin and anti-digoxin antibodies biotin or biotin analogues (e.g. aminobiotin, iminobiotin or desthiobiotin)/avidin or streptavidin, sugar/lectin enzyme and cofactor folic acid/folate double stranded oligonucleotides that selectively bind to proteins/, transcription factors, nucleic acid or nucleic acid analogue/complementary nucleic acid, receptor/ligand, e.g., steroid hormone receptor/steroid hormone It will be understood that the term "first" and "second" member of a binding pair is relative and that each of the above members can be seen as first or second members of the binding pair. In a preferred embodiment, the first member of a binding pair is glutathione and the second member of the binding pair is glutathione-S-transferase (GST).

The first and second members of the binding may be introduced in the cell using standard procedures for delivering a nucleic acid to the interior of the cell, (see sections 9.1 to 9.5 in Ausubel, F. M. et al., Current Protocols in Molecular Biology, John Wiley & Sons Inc; ringbou edition, 2003). In particular, the cells can be transfected by means of precipitating DNA with calcium phosphate, DEAE-dextran, polybrene, electroporation, microinjection, liposome-mediated fusion, lipofection, infection by retrovirus and biolistic transfection.

According to the invention, it is also possible to treat cells under conditions promoting protein turnover and hence leading to an increase in ubiquitylation. Illustrative, non limitative, ways of stimulating such ubiquitylation include stimulation with TNFα or UV irradiation (see Example 1 of the present invention). Indeed, inventors have shown that for the analysis of ubiquitylated IκBα, cells can be treated with TNFα to promote stimulation of ubiquitylated forms of this molecule. In another particular case, said cells can be stimulated by means of treatment with UV irradiation.

In a particular embodiment of the invention, said ubiquitylation signal present in the protein is selected from an artificial or a naturally occurring ubiquitylation sequence. As used herein, the term "ubiquitylation sequence" refers to an amino acid sequence present in said protein which is recognized by the corresponding ubiquitin activating enzyme, ubiquitin conjugating enzyme, and ubiquitin ligase and that induces the attachment of ubiquitin to said protein. Thus, in a preferred embodiment of the invention, the method comprises maintaining said cell in conditions allowing the attachment of said ubiquitin to said protein comprising a ubiquitylation signal. Illustrative, non limitative, examples of said ubiquitylation signals which are included within the scope of the present invention include (i) the BIO sequence which is a 75 amino-acid sequence derived from a *Propionibacterium shermanii* transcarboxylase that is efficiently biotinylated in vivo in yeast and mammalian cells (Tagwerker, C. et al. 2006. Mol and Cell proteomics, April; 5(4):737-48) and (ii) a N-terminal segment or substrate which is recognized and cleaved to form an activated substrate of the Ub-dependent N-end rule pathway (activated fragment) which is recognized through exposed destabilizing N-terminal residue. The degradation signal for ubiquitylation via the N-end rule pathways is termed an N-degron and comprises the primary destabilizing N-terminal residue and an internal lysine which is the site of ubiquitylation. Destabilizing N-terminal residues can be generated through proteolytic cleavages of specific proteins and other N-terminal modifications which reveal destabilizing residues at the new N-terminus. The residues that are exposed or modified to reveal an N-degron have been termed a pre-N-degron or pro-N-degron. For example, Sindbis virus RNA polymerase is produced during viral infection through site-specific cleavage of the viral polyprotein precursor and carries an N-terminal Tyr that has been shown in rabbit reticulocyte lysates to target the protein for ubiquitylation via the N-end rule pathway (deGroot et al., 1991, Proc. Natl. Acad. Sci. USA., 88: 8967-8971). Another example is RGS4, whose N-terminal degradation signal is generated through a series of N-terminal modifications including (1) removal of N-terminal Met and exposure of Cys-2 at the N-terminus, (2) oxidation of Cys-2 into cysteic acid, and (3) conjugation of Arg to the N-terminus of the protein (Kwon et al., 2002, Science, 297: 96-99).

As explained above, since many ubiquitylated proteins are rapidly turned over by proteasomes, when performing the method of the invention it is useful to treat cells with an inhibitor of the proteasome before analysis to preserve the ubiquitylated forms. Thus, in a particular embodiment, the method of the invention comprises an additional step previous to step ii), i.e., previous to the lysing and recovering step, wherein said cell is pre-treated with a proteasome inhibitor as explained before. As an illustrative, non limitative, way of blocking the catalytic activity of the proteasome without resulting in toxicity for the cells, cells can be pre-treated with the proteasome inhibitor MG132 as described in the example accompanying the present invention.

Once the cell has been maintained under conditions adequate for expression of the first and second gene constructs and adequate for the interaction between the UBD encoded by the first gene construct and the ubiquitin added to the ubiquitylation signal, the cells are lysed. Lysis can be carried out by means of any conventional method known in the state of the art. Indeed, many techniques are available for the disruption of cells, including physical and detergent-based methods. Clearly, the technique chosen for the disruption of cells, whether physical or detergent-based, must take into consideration the origin of the cells or tissues being examined and the inherent ease or difficulty in disrupting their outer layer(s). Rupture of the cells is carried out using any suitable method known in the art such as high pressure, nitrogen cavitation, osmotic shock using a hypotonic buffer, treatment with ultrasounds, mechanical homogeneisation, enzymolytic tissue disruption methods, sonication and the like. For example, cell lysis can be performed by sonication as explained in the Example of the present invention.

In a particular embodiment, said first gene construct encodes a polypeptide comprising at least two ubiquitin binding domains, wherein said ubiquitin binding domains are linked to each other via a non-naturally occurring intervening amino acid sequence.

In another particular embodiment of the invention, the second gene construct encodes for a polypeptide which is normally not expressed in the host cell.

In a particular embodiment of the invention, the recovering step is carried out by means of using an affinity column coupled to the second member of the binding pair.

In another aspect, the invention refers to a kit, hereinafter kit of the invention, comprising the polypeptide of the invention. In the present invention, a "kit" is understood as a product containing the different reagents for the carrying out the methods according to the present invention. The kits of the invention may comprise a packing which allows maintaining the reagents within determined limits. Suitable materials for preparing such packings include glass, plastic (polyethylene, polypropylene, polycarbonate and the like), bottles, vials, paper, sachets and the like. The kit of the invention can additionally contain instructions for using the reagents in the method of the invention. Said instructions can be found in the form of printed material or in the form of an electronic support which can store instructions such that they can be read by a subject, such as electronic storage media (magnetic disks, tapes and the like), optical media (CD-ROM, DVD) and the like. The media can additionally or alternatively contain Internet websites providing said instructions. In a particular embodiment, said kit further comprises a solid support. In a more particular embodiment, said support is agarose.

In Vitro Method for the Identification of Ubiquitylated Proteins.

The authors of the present invention have observed that the expression of the polypeptides of the invention in a cell results in the accumulation of polyubiquitylated proteins in the cell. This effect is due both to an inhibition of the proteasomal degradation of the polyubiquitylated polypeptides as well as to an inhibition of the deconjugation mediated by deubiquitylating enzymes (DUBs) (see example 6). This finding allows the use of the polypeptides of the invention to enrich the cell in ubiquitylated proteins which can then be purified and further characterised. Thus, in another aspect, the invention refers to an in vitro method for the identification of ubiquitylated proteins which comprises (i) introducing into a cell a gene construct encoding a polypeptide of the invention,
(ii) maintaining said cell under conditions adequate for the expression of said gene construct and adequate for the inhibition of the proteasomal and deubiquitylating proteins of the cell by the polypeptide of the invention and
(iii) identifying those proteins which contain one or more ubiquitin moieties.

Step (i) of the method of the invention comprises introducing into a cell a gene construct encoding a polypeptide of the invention, i.e. a polypeptide comprising at least two ubiquitin binding domains, wherein said ubiquitin binding domains are linked to each other via a non-naturally occurring intervening amino acid sequence. The introducing step is carried out essentially as described previously in the context of the in vitro method for the isolation of a protein comprising an ubiquitylation signal. The cells used in the present method can be cells derived from a disease tissue of a patient like for example tissue from a disease caused by a deregulation of the proteasome degradation, from a deubiquitylation related disorder or from a cancer. Examples of cancer are: bile duct cancer, brain cancer, breast cancer, cervical cancer, choriocarcinoma, colon cancer, endometrial cancer, esophageal cancer, stomach cancer, intraepithelial neoplasms, lymphomas, liver cancer, lung cancer (e.g., small cell and non-small cell lung cancer), melanoma, neuroblastomas, mouth cancer, ovarian cancer, pancreatic cancer, prostate cancer, rectal cancer, sarcomas, skin cancer, testicular cancer, thyroid cancer, and renal cancer, as well as tissue from other carcinomas and sarcomas. The cells used in the present method can also be stable cells lines like for example the cancer cell lines Huh7, PLC/PRF/5, Hep3B, HepG2, Hela, A549 and the like.

In step (ii) the cell is maintained under conditions adequate for the expression of the gene construct inserted in the cell in step (i). The expression of the polypeptide results in the inhibition of the degradation of the ubiquitylated proteins due to an inhibition of their degradation in the proteasome as well as to an inhibition of their deconjugation by DUBs.

Lastly, in step (iii) the ubiquitylated proteins which accumulate in the cell in the presence of the polypeptides of the invention can then be isolated and characterised. Depending on the source, the cells have to be lysed in order to recover the ubiquitylated proteins. There are several methods to achieve this including, without limitation, repeated freezing and thawing, sonication, homogenization by high pressure or permeabilization by organic solvents. The method of choice depends on how fragile the protein is and how sturdy the cells are. After this extraction process soluble proteins will be in the solvent, and can be separated from cell membranes, DNA etc. by centrifugation. The extraction process also extracts proteases, which will start digesting the proteins in the solution. If the protein is sensitive to proteolysis, it is usually desirable to proceed quickly, and keep the extract cooled, to slow down proteolysis.

The characterisation of the ubiquitylated proteins in the cell lysate can be carried out using any method known in the art. Preferably, the ubiquitylated proteins are first purified or using protein purification methods known to the skilled person such as precipitation and differential solubilisation (e.g. for separating proteins from different cell compartments), ultracentrifugation, chromatographic methods (size exclusion chromatography, ion exchange chromatography, affinity chromatography, metal binding, immunoaffinity chromatography, HPLC) and Pull-down assays, etc (see "Protein Purification", 1982 Springer-Verlag, N.Y and Pascal Bailon, et al, 2000 An Overview of Affinity Chromatography, Humana Press).

As a person skilled in the art would understand, the polypeptides of the invention show a high affinity towards polyubiquitylated proteins. This association can then be used for increasing the specificity of the recovery of the polyubiquitylated proteins. Thus, as a skilled person will understand, if the polypeptide of the invention further comprises a tag, it will be possible to purify the complexes comprising the polyubiquitylated proteins and the polypeptides of the invention by immunoaffinity chromatography or pull down assays.

In other embodiment, the isolation of the ubiquitylated proteins is performed using an anti-ubiquitin antibody. In a more preferred embodiment the isolation of the ubiquitylated proteins is performed by means of affinity chromatography wherein the ubiquitylated proteins are isolated using an anti-ubiquitin antibody immobilized on a column.

As a person skilled in the art would understand a combination of the above described methods and the different tags can be used.

As the skilled person understands, multiple approaches can be used to identify the ubiquitylated protein composition of a sample. In a preferred embodiment, the proteins are fractionated using gel electrophoresis. In a still more preferred embodiment, the gel electrophoresis is a two-dimensional gel electrophoresis.

In one embodiment, the ubiquitylated proteins protected from deubiquitylation and degradation as disclosed herein, and/or their polypeptide levels in the tissue sample can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118, 937 and U.S. Pat. No. 5,045,694.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4th ed. Vol. 15 (John Wiley AND Sons, New York 1995), pp. 1071-1094.

Protein Interaction Methods

In another aspect, the invention refers to a method for real time protein interaction analysis in vivo which comprises
- a) the introduction of a first gene construct encoding a protein comprising a polypeptide of the invention, a first member of a binding pair and a detectable tag, and a second gene construct encoding a protein comprising a ubiquitylation signal and a detectable tag into a cell in conditions allowing the expression of said gene constructs and in conditions allowing the interaction between the UBD of the protein encoded by the first gene construct and the ubiquitin added to the ubiquitylation signal of the protein encoded by the second construct and
- b) maintaining the cells under conditions allowing the expression of said gene constructs and allowing the interaction between the UBD of the protein encoded by the first gene construct and the ubiquitin added to the ubiquitylation signal of the protein encoded by the second construct and
- c) the measuring the interaction of both proteins using the detectable tags.

The introduction of the first gene construct and the second gene constructed can be performed as described before.

The measuring the interaction of both proteins using the detectable tags can be done using for example FRET (Fluorescence resonance energy transfer). The detectable tags for measuring the interaction with FRET should be fluorophores like fluorescent moieties (e.g., fluoresceine, rhodamine, phycoerythrin, coumarin, oxazine, resorufin, cyanine and derivatives thereof.), luminescent moieties (e.g., Qdot™ nanoparticles supplied by the Quantum Dot Corporation, Palo Alto, Calif.), fluorescent proteins (GFP, YFP, etc), etc. One of the fluorophores is the donor and the other the acceptor (see Zal T. et al., 2008, Adv. Exp. Med. Biol. 640:183-97). An increase in the emission of the acceptor indicates that the both proteins are interacting. Microscopy methods (Gordon, G W et al; 1998 Biophys J. May; 74:2702-13.) and FACS analysis can be used for measuring FRET.

In another aspect, the invention refers to a method for real time protein interaction analysis in vitro which comprises,
- (i) immobilizing in a surface a polypeptide comprising at least two ubiquitin binding domains, wherein said ubiquitin binding domains are linked to each other via a non-naturally occurring intervening amino acid sequence,
- (ii) contacting said immobilised polypeptide with an ubiquitylated protein which comprises a detectable tag in conditions allowing the interaction between the UBD of the first protein and the ubiquitin molecules of the second protein, and
- (iii) measuring of the interaction of the both proteins.

In an illustrative way, such real time protein interaction analysis is carried out by means of Surface Plasmon Resonance. The inventors have used the BIAcore 3000 system, which is an instrument that uses SPR technology for measuring the interactions of macromolecules with each other, and with small ligands. One of the ligands is immobilized on carboxymethylated dextran over a gold surface, while the second partner (analyte) is captured as it flows over the immobilized ligand surface. Most ligands can be directly immobilized onto the surface of the chip via amino groups, carbohydrate moieties, or sulfhydryl groups. Others are immobilized indirectly through the use of biotinylation of the ligand (such as biotinylated peptides or oligonucleotides), or through immobilized monoclonal antibodies (such as anti-GST). Typical amounts of a protein ligand needed for an immobilization reaction is about 1 µg. The immobilized ligands are remarkably resilient and maintain their biological activity. The bound analytes can be stripped from the immobilized ligand without affecting its activity to allow many cycles of binding and regeneration on the same immobilized surface. Interaction is detected via SPR, in real time, at high sensitivity, without the use of radioactivity. In a preferred embodiment, the binding studies are carried out by immobilization of anti-GST monoclonal antibodies followed by binding of fusion proteins comprising GST and a variable number of UBDs (see FIG. 5).

In Vitro Method for Inhibiting Deubiquitylation and Proteasomal Degradation of Ubiquitylated Proteins.

In another aspect, the invention refers to an in vitro method for inhibiting deubiquitylation and proteasomal degradation of ubiquitylated proteins which comprises
(i) introducing into a cell a first gene construct encoding a protein comprising a polypeptide as defined in claims 1 or 2, a first member of a binding pair and a detectable tag and a second gene construct encoding a protein comprising a ubiquitylation signal and a detectable tag into a cell,
(ii) maintaining the cells under conditions allowing the expression of said gene constructs and allowing the interaction between the UBD of the protein encoded by the first gene construct and the ubiquitin added to the ubiquitylation signal of the protein encoded by the second construct.

The introduction of the gene construct in the cell can be performed as described before.

In Vitro Method for the Identification of Ubiquitylated Proteins.

The authors of the present invention have observed that the expression of the polypeptides of the invention in a cell results in the accumulation of polyubiquitylated proteins in the cell. This effect is due both to an inhibition of the proteasomal degradation of the polyubiquitylated polypeptides as well as to an inhibition of the deconjugation mediated by deubiquitylating enzymes (DUBs) (see example 6). This finding allows the use of the polypeptides of the invention to enrich the cell in ubiquitylated proteins which can then be purified and further characterised. Thus, in another aspect, the invention refers to an in vitro method for the identification of ubiquitylated proteins which comprises
(i) introducing into a cell a gene construct encoding a polypeptide of the invention,
(ii) maintaining said cell under conditions adequate for the expression of said gene construct and adequate for the inhibition of the proteasomal and deubiquitylating proteins of the cell by the polypeptide of the invention and
(iii) identifying those proteins which contain one or more ubiquitin moieties.

Step (i) of the method of the invention comprises introducing into a cell a gene construct encoding a polypeptide of the invention, i.e. a polypeptide comprising at least two ubiquitin binding domains, wherein said ubiquitin binding domains are linked to each other via a non-naturally occurring intervening amino acid sequence. The introducing step is carried out essentially as described previously in the context of the in vitro method for the isolation of a protein comprising an ubiquitylation signal. The cells used in the present method can be cells derived from a disease tissue of a patient like for example tissue from a disease caused by a deregulation of the proteasome degradation, from a deubiquitylation related disorder or from a cancer. Examples of cancer are: bile duct cancer, brain cancer, breast cancer, cervical cancer, choriocarcinoma, colon cancer, endometrial cancer, esophageal cancer, stomach cancer, intraepithelial neoplasms, lymphomas, liver cancer, lung cancer (e.g., small cell and non-small cell lung cancer), melanoma, neuroblastomas, mouth cancer, ovarian cancer, pancreatic cancer, prostate cancer, rectal cancer, sarcomas, skin cancer, testicular cancer, thyroid cancer, and renal cancer, as well as tissue from other carcinomas and sarcomas. The cells used in the present method can also be stable cells lines like for example the cancer cell lines Huh7, PLC/PRF/5, Hep3B, HepG2, Hela, A549 and the like.

In step (ii) the cell is maintained under conditions adequate for the expression of the gene construct inserted in the cell in step (i). The expression of the polypeptide results in the inhibition of the degradation of the ubiquitylated proteins due to an inhibition of their degradation in the proteasome as well as to an inhibition of their deconjugation by DUBs.

Lastly, in step (iii) the ubiquitylated proteins which accumulate in the cell in the presence of the polypeptides of the invention can then be isolated and characterised. Depending on the source, the cells have to be lysed in order to recover the ubiquitylated proteins. There are several methods to achieve this including, without limitation, repeated freezing and thawing, sonication, homogenization by high pressure or permeabilization by organic solvents. The method of choice depends on how fragile the protein is and how sturdy the cells are. After this extraction process soluble proteins will be in the solvent, and can be separated from cell membranes, DNA etc. by centrifugation. The extraction process also extracts proteases, which will start digesting the proteins in the solution. If the protein is sensitive to proteolysis, it is usually desirable to proceed quickly, and keep the extract cooled, to slow down proteolysis.

The characterisation of the ubiquitylated proteins in the cell lysate can be carried out using any method known in the art. Preferably, the ubiquitylated proteins are first purified or using protein purification methods known to the skilled person such as precipitation and differential solubilisation (e.g. for separating proteins from different cell compartments), ultracentrifugation, chromatographic methods (size exclusion chromatography, ion exchange chromatography, affinity chromatography, metal binding, immunoaffinity chromatography, HPLC) and Pull-down assays, etc (see "Protein Purification", 1982 Springer-Verlag, N.Y and Pascal Bailon, et al, 2000 An Overview of Affinity Chromatography, Humana Press).

As a person skilled in the art would understand, the polypeptides of the invention show a high affinity towards polyubiquitylated proteins. This association can then be used for increasing the specificity of the recovery of the polyubiquitylated proteins. Thus, as a skilled person will understand, if the polypeptide of the invention further comprises a tag, it will be possible to purify the complexes comprising the polyubiquitylated proteins and the polypeptides of the invention by immunoaffinity chromatography or pull down assays.

In other embodiment, the isolation of the ubiquitylated proteins is performed using an anti-ubiquitin antibody. In a more preferred embodiment the isolation of the ubiquitylated proteins is performed by means of affinity chromatography wherein the ubiquitylated proteins are isolated using an anti-ubiquitin antibody immobilized on a column.

As a person skilled in the art would understand a combination of the above described methods and the different tags can be used.

As the skilled person understands, multiple approaches can be used to identify the ubiquitylated protein composition of a sample. In a preferred embodiment, the proteins are fractionated using gel electrophoresis. In a still more preferred embodiment, the gel electrophoresis is a two-dimensional gel electrophoresis.

In one embodiment, the ubiquitylated proteins protected from deubiquitylation and degradation as disclosed herein, and/or their polypeptide levels in the tissue sample can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 and U.S. Pat. No. 5,045,694.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4th ed. Vol. 15 (John Wiley AND Sons, New York 1995), pp. 1071-1094.

In another aspect, the invention refers to an in vitro method for the identification of proteins which are ubiquitylated in response to a signal which comprises
  (i) introducing into a first and a second cell population a gene construct encoding a polypeptide comprising at least two ubiquitin binding domains, wherein said ubiquitin binding domains are linked to each other via a non-naturally occurring intervening amino acid sequence,
  (ii) maintaining the cells of said first and second population under conditions allowing the expression of said gene construct,
  (iii) applying to the first cell population the signal whose effect in ubiquitylation is to be studied and
  (iv) characterising the proteins which are differentially ubiquitylated in said first cell population in comparison with a second cell population.

The term "signal" as used herein refers to any stimuli or condition which, when applied to a cell, may result in the modification of the levels of ubiquitylated proteins in said cells (see example 11b). Examples of these treatments could be the changing of the culturing conditions (e.g. hypoxia) or the treatment with a compound that could modify the levels of ubiquitylated proteins in said cells. Moreover, a signal can be used that mimics a situation occurring under disease conditions. The cells that can be used in the present method are the same as described before. The cells used in the present method can also be stable cells lines like, for example, the cancer cell lines Huh7, PLC/PRF/5, Hep3B, HepG2, Hela, A549, etc.

The introduction into a cell of the gene construct in step (i), the lysis of the cells, the purification of the proteins and the identification of the ubiquitylated proteins can be done as described before.

The polypeptide of the invention can be used for the purification and identification of ubiquitylated proteins from animal tissues as described in example 12 of the present invention.

Therapeutic Methods of the Invention

In another aspect, the invention refers to a method for the treatment of a deubiquitylation related disorder which comprises the administration of the polypeptide of the invention.

As used herein, the term "deubiquitylation related disorder" includes any disorder, disease or condition which is caused or characterized by an increase or decrease in the deubiquitylating activity.

"Deubiquitylating activity" refers to any biological activity associated with a deubiquitylating agent known in the art, for example, a cellular process, catalytic property, and more specifically, the binding, release, or cleavage of an ubiquitin moiety from an ubiquitin complex. Examples of cellular processes involving deubiquitylating agents include, but are not limited to, the disassembly of polyubiquitin to recycle ubiquitin; releasing of ubiquitin from 26S proteasome substrates, releasing of monomeric ubiquitin from ubiquitin fusion polypeptide precursors, reversal of regulatory ubiquitylation, editing of ubiquitylated proteins that have been inappropriately ubiquitylated proteins, and regeneration of active ubiquitin from adducts with small nucleophiles (e.g., glutathione) that may be generated by side reactions (Wilkinson and Hoschstrasser, 1998, incorporated herein by reference). Generally, such deubiquitylating activity affects the level of free ubiquitin and other specific proteins in the cell (D'Andrea et al. (1998) Critical Reviews In Biochemistry and Molecular Biology 33: 337-352,). Examples of such diseases are cancer, cardiovascular diseases, neurological disorders, cachexia and muscle wasting.

The administration of the polypeptide of the invention to the subject suffering a deubiquitylation related disorder can be done using Genetic therapy, which is based on inserting therapeutic genes into cells by means of ex vivo or in vivo techniques. In literature, suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. The polynucleotide codifying the polypeptide of the invention can be designed for direct insertion or by insertion through liposomes or viral vectors (for example, adenoviral or retroviral vectors) in the cell. Preferably, said cell is a cell of the germinal line, an embryonic cell or egg cell or derived from the same, more preferably said cell is a core cell. As is clear from the foregoing, it is preferred that in the use of the invention, the sequence of nucleic acid be operationally united to the regulatory elements that permit the expression and/or the integration of the polypeptides of the invention into specific cells. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient.

In another aspect, the invention refers to a method for the treatment of a disease caused by a deregulation of the proteasome degradation of at least one ubiquitylated polypeptide which comprises the administration to a subject in need thereof of the polypeptides as described in the invention.

As used herein, the term "disease caused by a deregulation of the proteasome degradation" includes any disorder, disease or condition which is caused or characterized by an increase or decrease degradation of one or more proteins via the proteosomal degradation.

Relevant "disease caused by a deregulation of the proteasome degradation" include inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis)), vascular proliferative disorders (e.g., atherosclerosis, restenosis), proliferative ocular disorders (e.g., diabetic retinopathy), benign proliferative disorders (e.g., hemangiomas), autoimmune diseases (e.g., multiple sclerosis, tissue and organ rejection), as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and blood borne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed proteasome inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed proteasome inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

The administration of the polypeptide of the invention can be performed as described before.

The invention is hereby explained by the following examples which should not be construed as limiting but rather as merely illustrative of the invention.

EXAMPLES

I. Materials and Methods 1.1. Molecular Cloning.

DNA fragments encoding the various UBA and UIM motifs were obtained by PCR and cloned into the PGEX-6P1 (Amersham) vector modified with a linker which introduces in frame a His6 tag upstream and a SV5 epitope downstream the multi-cloning site. Such modifications of the vector allow the recognition of the protein by specific antibodies. Up to four copies of each UBD were included in these constructs, each of them separated by a poly glycine spacer. PCR DNA fragments were cloned in a 5'-3' orientation using specific primers as follows:

```
p62 primers
                                       (SEQ ID NO: 18)
5' CCGCTCGAGGGAGGAGGTCCGCGGCTGATTGAGTCC 3'
and
                                       (SEQ ID NO 19)
5' CGCGTCGACGCCGCCACCGGGATGCTTTGAATACTGGATG 3';

hHR23 UBA1 primers
                                       (SEQ ID NO: 20)
5' CGCGTCGACGCCGCCACCGGGATGCTTTGAATACTGGATG 3'

(SEQ ID NO: 21)
5' CGCGGATCCGGTGCCGCCAGAACCGTGTTCCGGCTCG 3'
```

-continued hHR23A UBA2 primers:
(SEQ ID NO: 22)
5' GGAAGATCTGGTGGAGGTTACATCCAGGTGACGCCG 3'

(SEQ ID NO: 23)
5' -CGCGGATCCGCCGCCCTCGTCATCAAAGTTCTGACTC 3'

Ubiquilin1 primers
(SEQ ID NO: 24)
5' GGAAGATCTGGAGGTGGAGTAAATCCTCAGCTACAGAATCCAG 3'

(SEQ ID NO: 25)
5' CGCGGATCCTCCACCTCCTGATGGCTGGGAGCCCAGTAAC 3'

S5a primers
(SEQ ID NO: 26)
5' CCGCTCGAGGGAGGAGATCCCAGTGCTGATCCTGAG 3'

(SEQ ID NO: 27)
5' CGCGTCGACGCCGCCTGCTCCCTGCAGGGACATC 3'

The same constructs were sub-cloned into a tet-on inducible vector (Clontech) for expression in eukaryote cells. Table I summarises the different constructs used in the present invention.

TABLE I

List of all polynucleotide and polypeptide sequences used in the present invention.

| SEQ ID NO: | Chemistry | Nature |
|---|---|---|
| 1 | Polypeptide | TUBE comprising 4 hHR23a UBA-1 domains |
| 2 | Polypeptide | TUBE comprising 4 hHR23a UBA-2 domains |
| 3 | Polypeptide | TUBE comprising 4 p62 UBA domains |
| 4 | Polypeptide | TUBE comprising 4 ubiquilin-1UBA domains |
| 5 | Polypeptide | TUBE comprising 4 S5a UIM-1 domains and 4 S5a UIM-2 domains |
| 6 | Nucleic acid | Polynucleotide encoding SEQ ID NO: 1 |
| 7 | Nucleic acid | Polynucleotide encoding SEQ ID NO: 2 |
| 8 | Nucleic acid | Polynucleotide encoding SEQ ID NO: 3 |
| 9 | Nucleic acid | Polynucleotide encoding SEQ ID NO: 4 |
| 10 | Nucleic acid | Polynucleotide encoding SEQ ID NO: 5 |
| 11 | Polypeptide | Linker region |
| 12 | Polypeptide | hHR23a UBA-1 domain |
| 13 | Polypeptide | hHR23a UBA-2 domain |
| 14 | Polypeptide | p62 UBA domain |
| 15 | Polypeptide | Ubiquilin-1 UBA domain |
| 16 | Polypeptide | S5a UIM-1 domain |
| 17 | Polypeptide | S5a UIM-2 domain |

1.2. Protein Expression.

To generate affinity columns, pGEX vector encoding the constructs of the invention were expressed according to standard procedures provided by the manufacturer using the *E. coli* C43 (DE3) strain.

1.3. Affinity Columns.

The recombinant polypeptides of the invention produced in bacteria were retained on agarose beads coupled to glutathione (Sigma product G4510). To purify ubiquitylated proteins from cell extracts, cells were first pre-treated during 3 hours with 20 μM of the proteasome inhibitor MG132 (BIOMOL) before 3 hours of stimulation with 20 ng/ml of TNFα. Lysis was performed by sonication using a PBS buffer containing 2 mM benzamidine. After sonication 1% Triton X-100 was added and gently mixed. Supernatant was recovered after centrifugation to 20,000 rpm and incubated with the Agarose-Glutathione-polypeptides for 2 hours at 4° C. Unbound material was recovered for analysis and beads were washed 4 times with one column volume of the same buffer. Washed columns were eluted with disruption boiling buffer 3× and bound and unbound fractions analysed by Western blot with an anti-IκBα or anti-histidine. For p53 experiments, conditions are quite similar, except that p53 knock-out cells transiently expressing WTp53 were used as source of ubiquitylated forms of this tumour suppressor. Cells were pre-treated during 3 hours with proteasome inhibitors before lysis and immediate incubation with agarose-bound polypeptide comprising ubiquitin binding domains of p62.

1.4. BiaCore Measurements.

To measure real-time interactions, all experiments were performed with a BiaCore 3000 instrument, at 25° C., using HBS EP (0.01 B M HEPES pH 7.4, 0.15 M NaCl, 3 mM EDTA, 0.005% surfactant P20) (BiaCore) as running buffer. Anti GST antibody (BiaCore) was covalently immobilized on a CM5 chip (carboxy methylated dextran) from BiaCore with a density of approximately 9000 resonance units (RU≈pg·mm-2), using standard amino-coupling techniques and reagents (NHS, EDC, ethanolamine) from BiaCore. Purified GST-tagged polypeptide comprising ubiquitin binding domains of p62 protein and GST were diluted in running buffer and captured to similar levels in different flow cells. Single and tandem GST-fused UBA domains were captured on the sensor chip at low (30-55 RU) and high (130-220 RU) densities.

Prior to analysis, ubiquitin (SIGMA) was additionally purified and concentrated by repeated washing with PBS using centrifugal filters with nominal molecular weight cut-off of 3 kDa (Millipore).

A randomized injection of a ubiquitin dilution series (4 μM, 20 μM, 100 μM and 500 μM) over the flow cells was performed using BiaCore automated method language programming.

Running buffer injections were used as blank injections. Injected volume was 50 μl, and the flow rate was set to 25 μl/min. Regeneration of the anti GST antibody was performed by an injection of 10 mM glycine pH 2.2, followed by 0.1% SDS.

Mono-ubiquitin (Sigma Aldrich), K48 or K63 tetra-ubiquitin (Boston Biochem) or the ubiquitin-like molecules SUMO-1, -2, -3 (produced as previously described (Rodriguez et al., 1999 *Embo J.* 18, 6455-6461)) and NEDD8 (Boston Biochem) were then injected for 30 s (short injections) or 1500 s (long injections) over the single UBA or TUBE surfaces at a flow rate of 30 or 10 μl/min respectively. All injections were done as randomized duplicates, and each experiment was repeated in triplicate. All the experimental profiles were double referenced using the Scrubber 2.0 software (BioLogic Software), i.e. both the signals from a His6-GST-SV5 reference surface and from blank experiments (running buffer instead of protein) were subtracted. The steady-state responses (Req) were estimated by averaging the signal monitored during the last 15 seconds of each injection. The Req values were plotted against the concentration (C) of mono or tetra-ubiquitin and fitted using the following equation:

$$Req=(Rmax*C)/(Kd+C)$$

where Kd is the equilibrium dissociation constant and Rmax the maximal binding capacity of the surface.

Binding stoichiometries (n) were determined as the ratio $$[Rmax/M(Ub)]/[Rimmo/M(UBA)]$$

where M(Ub) and M(UBA) are respectively the molecular masses of ubiquitin (mono or tetra) and GST-UBA (single or tandem) and Rimmo the density of captured GST-UBA.

The dissociation profiles were analyzed using the following double-exponential function of time:

$$R=R1*e\text{-}koff\,1+R2*e\text{-}koff\,2$$

where koff1 and koff2 are respectively the dissociation rates of the first and the second dissociation phases, and R1 and R2 their corresponding amplitudes.

Half-lifes (t1/2) were calculated from the dissociation rates using the relation:

$$t1/2 = \ln 2/k_{off}$$

Data analysis was carried out using BiaEval (BiaCore) and Scrubber (BioLogic Software).

1.5 Cell Culture, Cell Lysis, In Vitro Degradation Assay and Immunodetection.

For all experiments, cells were grown in DMEM (Gibco) supplemented with 10% FBS and antibiotics. For IκBα experiments, HEK 293 cells were pre-treated for three hours with 20 μM MG132, and then stimulated with 10 ng/ml TNF-α. Three hours after TNF-α stimulation, cells were lysed and processed. For p53 experiments, p53 WT MCF-7 cells were pulsed for one hour with 10 μM doxorubicin, and lysed at the indicated time points. In all cases, cells were lysed for 15 minutes on ice in 50 mM sodium fluoride, 5 mM tetra-sodium pyrophosphate, 10 mM beta-glyceropyrophosphate, 1% Igepal CA-630, 2 mM EDTA, 20 mM Na2HPO4, 20 mM NaH2PO4, 1 mM Pefablock, 1.2 mg/ml. Complete protease inhibitor cocktail (Roche). This buffer was supplemented either with 400 μg/ml (7 μM) TUBEs or with 10 mM IAA/NEM. Lysates were clarified by cold centrifugation at 13.000 rpm for ten minutes, and added to 50 μl of glutathione agarose beads (Sigma Aldrich), either empty or pre-bound to GST-fusion proteins. In vitro transcribed/translated full-length p53 was incubated in a degradation mixture that contained: 40 mM Tris-HCl, pH 7.5, 5 mM MgCl2, 2 mM DTT, 0.5 mM ATP, 10 mM phosphocreatine, 1.6 mg/ml creatine phosphokinase, 200 μg/ml ubiquitin. 1 μg purified 26S proteasome or 3 μl of untreated rabbit reticulocyte lysate (as a source of the 26S proteasome) were then added. In vitro transcribed/translated MDM2 was supplemented to the reactions. The degradation mixture was incubated at 37° C. for 90 min. and the reaction was stopped by addition of SDS sample buffer.

Immunodetections were performed with the following primary antibodies: TUBEs—mouse monoclonal SV5 antibody (Serotec); p53—mouse monoclonal DO-1 (Santa Cruz Biotechnology); Mdm2—mouse monoclonal Ab5 (Calbiochem); poly-ubiquitin—FK1 mouse monoclonal (Biomol); IκBα—rabbit polyclonal (Santa Cruz Biotechnology); Sam68-rabbit polyclonal (Santa Cruz Biotechnology). Secondary antibodies were: rabbit anti-mouse polyclonal and goat anti-rabbit polyclonal (Jackson Immunoresearch).

Example 1

Cloning and Characterization of the TUBES

Figure 2:
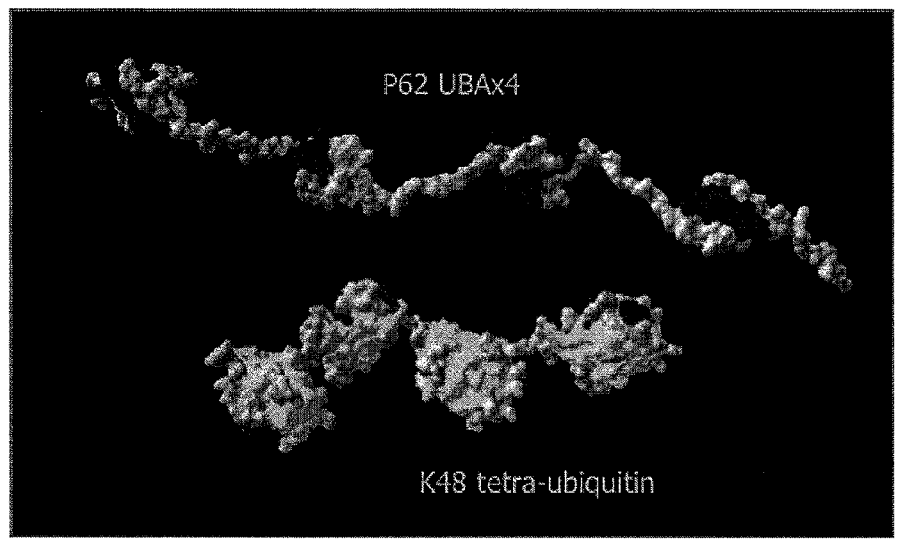
FIG. 2. Model of tetra-ubiquitin molecule interacting with the polypeptide of the invention comprising UBDs of p62 protein. Representation of a K48-mediated ubiquitin chain interacting with said polypeptide comprising 4 UBD.

In order to study whether proteins with multiple ubiquitin affinity motifs would show increased affinity towards ubiquitin-modified targets, proteins comprising multiple ubiquitin domains were constructed. In accordance with the resolved and published molecular structures for ubiquitin and the UBA domain of the prototype construct comprising the ubiquitin binding domains of p62 protein, a cooperative interaction between a tetraubiquitin molecule formed by K48 linkages and this ubiquitin trap could be expected (FIG. 2).

The gene constructs of the invention encoding one, two or four UBDs spaced by a flexible poly-glycine linker, were develop for this prototype using the UBA domain of the p62 ubiquitin trap as indicated in materials and methods and illustrated in FIG. 3. To facilitate the use of the corresponding polypeptides as affinity columns, the gene constructs were cloned into a vector expressing the GST protein (PGEX 6P1). This protein allows the purification of the polypeptides through a support of Glutathione—Sepharose. The principle and steps for the generation, purification and detection are illustrated in FIG. 3.

Example 2

Tandem-Coupling of UBA Domains Preserves their Ubiquitin-Binding Capacity

Figure 4A:
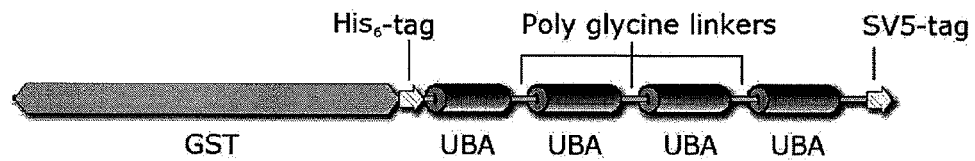
FIGS. 4A through 4C—(FIG. 4A) Cartoon illustrating the design of TUBEs. Each UBA domain is separated by a flexible linker of eight glycines. Figure is to scale.
Figure 4B:
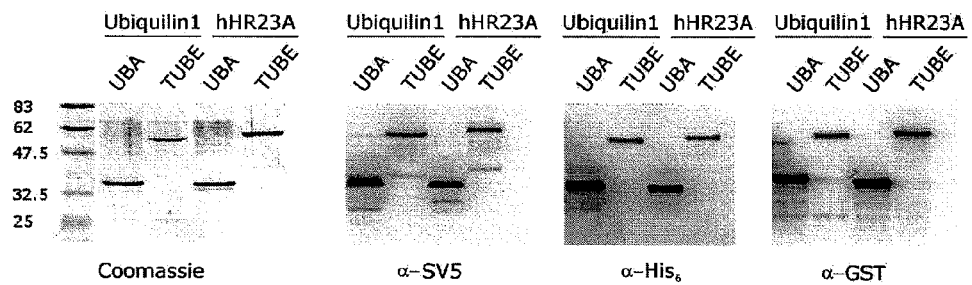

According to the present model of ubiquitin-mediated proteasomal degradation, four ubiquitin molecules are required to efficiently direct modified proteins to proteolysis. To increase the probability to isolate proteins modified with at least a tetra-ubiquitin chain, TUBEs were designed with four UBA domains, from the proteins ubiquilin1 and hHR23A (UBA1). To provide flexibility, an unstructured polyglycine linker was inserted between each domain (FIG. 4A). Several tags were added to facilitate TUBE detection with anti-GST, anti-His6 or anti-SV5 antibodies (FIG. 4B). To ensure that each UBA domain in the tandem retains its capacity to bind ubiquitin, surface plasmon resonance (SPR) experiments were performed to determine stoichiometric ratios and affinity constants. Ubiquilin1 and hHR23A TUBEs and individual UBA domains were captured through their GST tag on an anti-GST antibody sensorchip surface.

Figure 4C:
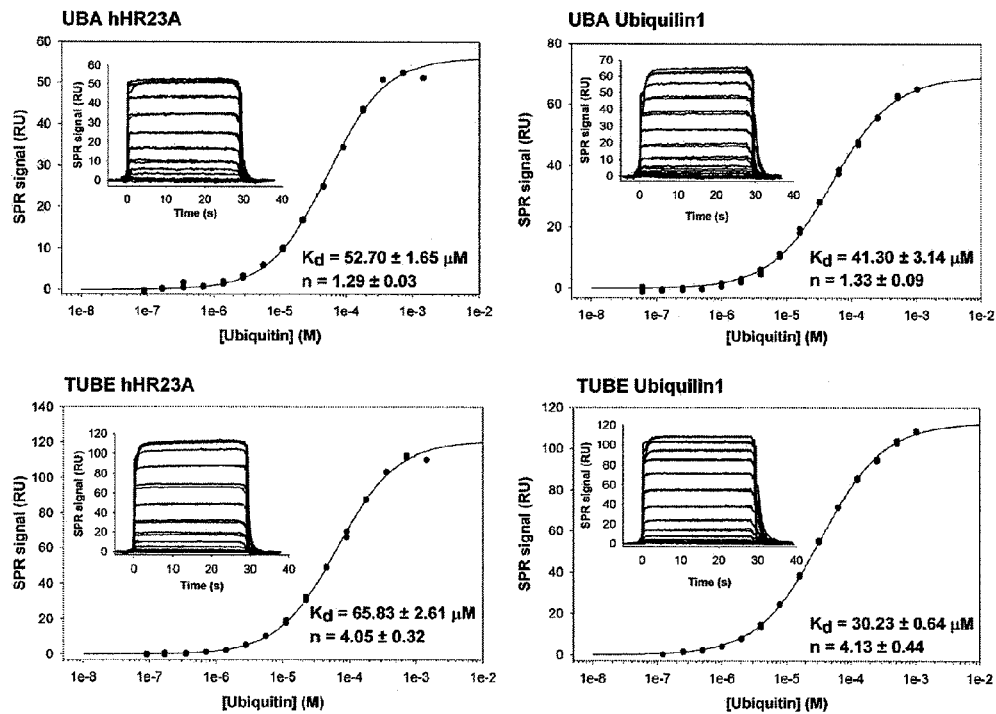

Ubiquitin was then flowed on the immobilized UBAs and TUBEs. The ubiquitin concentration dependence of the measured steady-state SPR signal was analyzed, showing that tandem-coupling of UBAs in TUBEs has little or no effect on their affinity for mono-ubiquitin. Interestingly, mono-ubiquitin appears to bind to TUBEs with a molar ratio of 4:1, in contrast to the 1:1 stoichiometry observed for single UBAs (FIG. 4C). Control experiments, in which the ubiquitin like molecules SUMO1, SUMO2, SUMO3 and NEDD8, were flowed over immobilized TUBEs, showed that no binding could be detected at concentrations as high as 200 μM, at which TUBEs were readily saturated by ubiquitin. These results showed that each individual UBA domain in the TUBEs was functional for mono-ubiquitin binding, as evidenced by the 4:1 interaction stoichiometry. Furthermore, tandem coupling of UBAs preserved both their affinity and their specificity for monoubiquitin.

In addition to the UBDs these vectors allows the expression of an N-terminal His6x tag and C-terminal epitope, which can be recognised by specific antibodies, allowing immunoprecipitation, immunodetection (ELISA and Western-blot) and sub-cellular distribution by indirect immunofluorescence. Another advantage of this construct is the PreScission protease cleavage site, permitting the removal of GST after incubation with this specific enzyme. This procedure could be used to analyse molecular interactions by surface plasmon resonance SPR (FIG. 5).

The capacity of the polypeptides of the invention comprising one, two or four UBA domains to interact with ubiquitin, was analysed using surface plasmon resonance technology (BIACORE 3000). The results indicate that the capacity of interaction of ubiquitin with the polypeptides of the invention, increase with the number of UBA copies expressed. The observed increase is proportional, as four and six times more binding was obtained with 2 and 4 UBA copies respectively (FIGS. 5A through 5C and FIGS. 8A through 8B).

Example 3

TUBEs Show Superior Binding to Poly-Ubiquitin

The hypothesis of a synergistic binding mode of tandem UBA domains to poly-ubiquitin was examined using K48 and K63 linked tetra-ubiquitin.

Figure 6A:
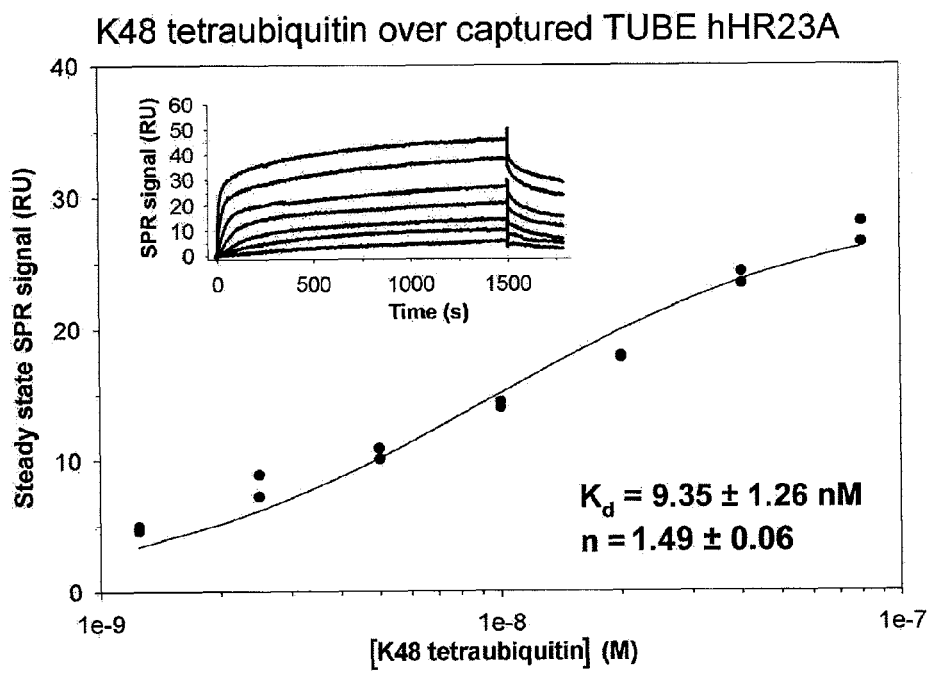
FIGS. 6A through 6F. TUBEs show enhanced binding to tetra-ubiquitin.
Figure 6B:
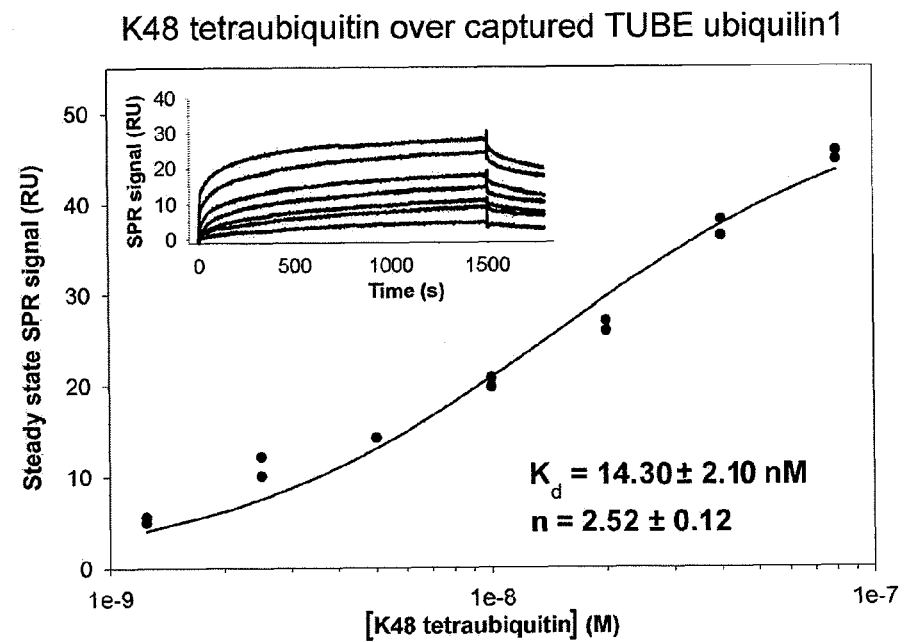
Figure 6C:
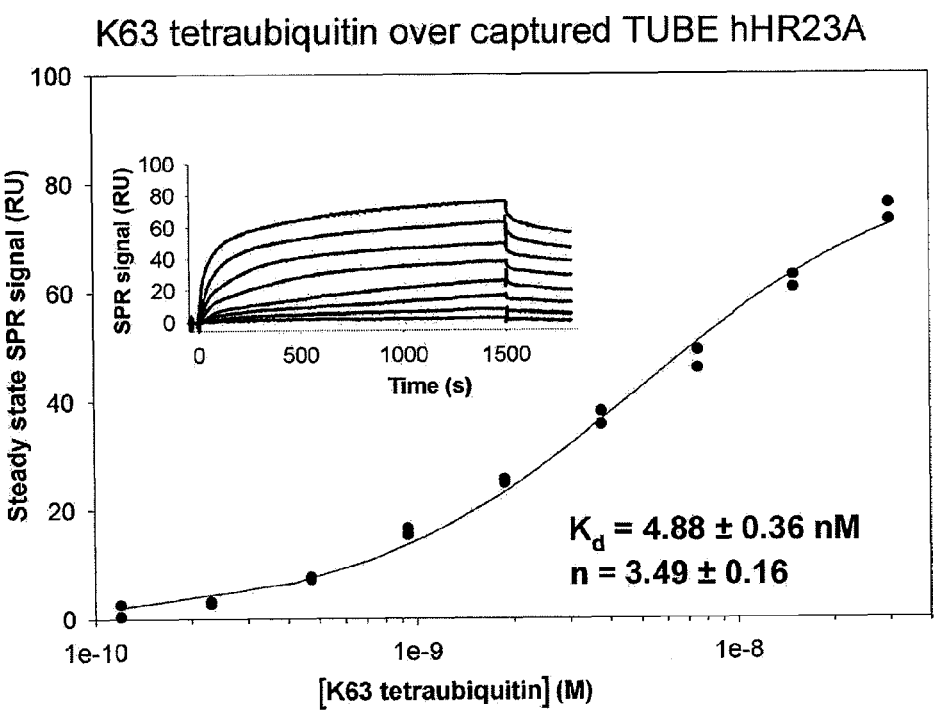
Figure 6D:
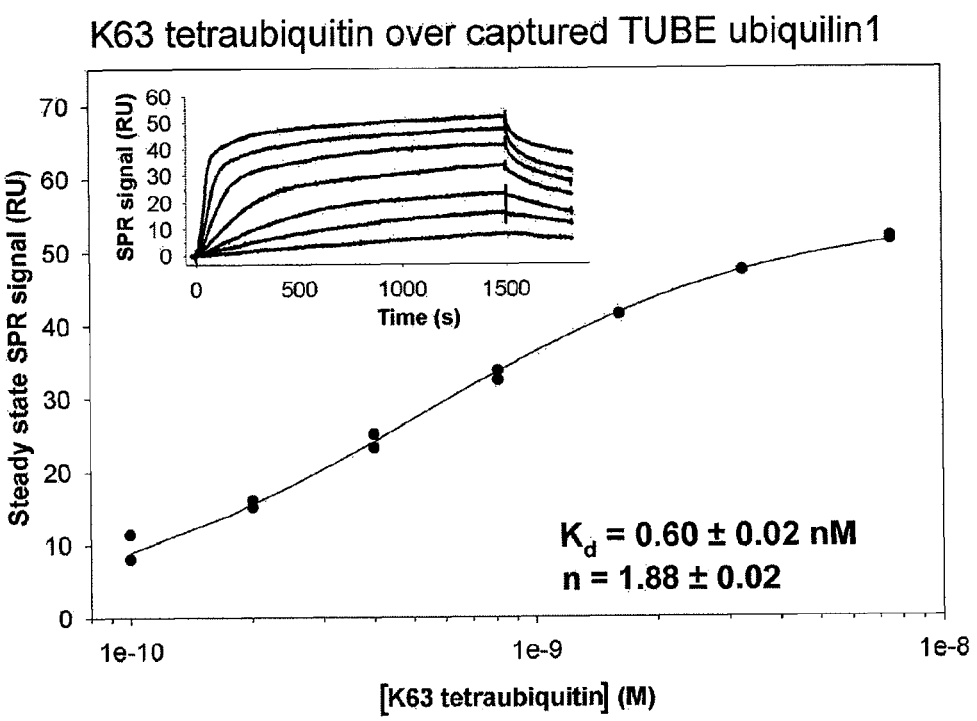
Figure 6E:
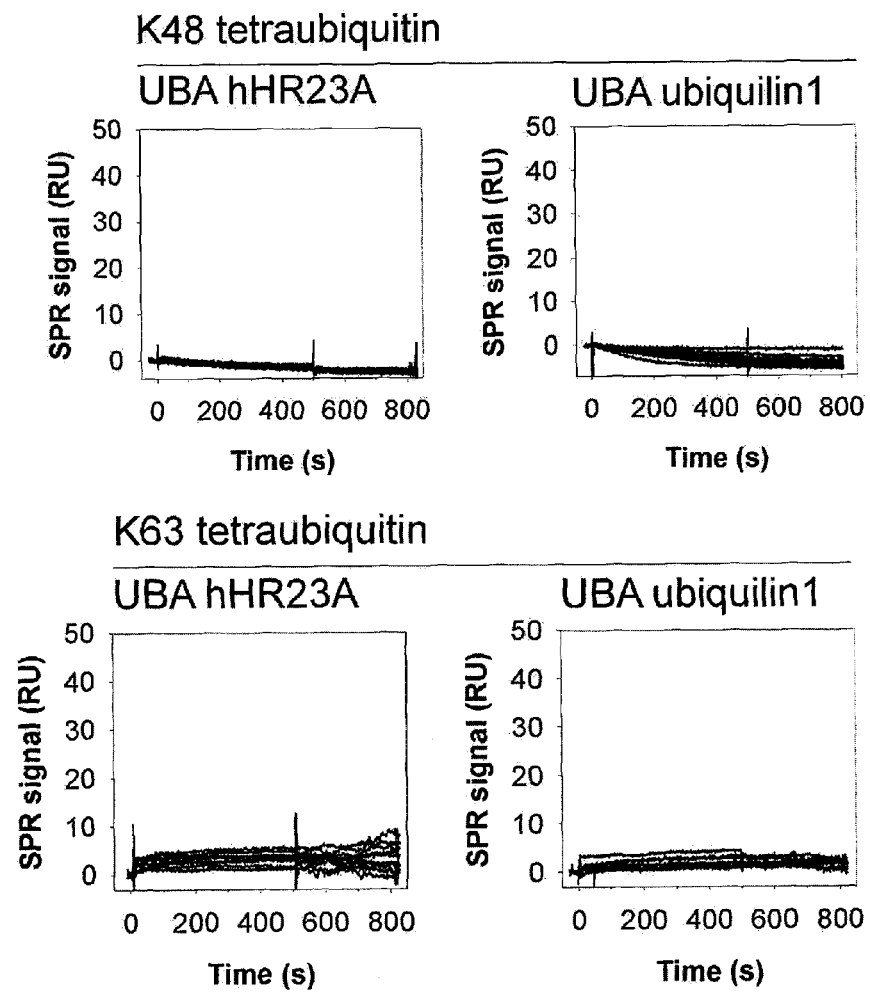

To determine accurately the global affinity of tetra-ubiquitin for the hHR23A and ubiquilin1 TUBEs, the tetra-ubiquitin concentration dependence of the steady-state SPR signal measured on low density surfaces after long injection times (FIGS. 6A, 6B, 6C, 6D) was analyzed. The calculated equilibrium dissociation constants (KD), in the nanomolar range, show 80 to 900-fold increases compared to reported values for single UBA domains (Raasi et al., 2005. Nat Struct Mol Biol, 12, 708-714.) (Table II). Further, no significant interaction of K48 and K63 tetra-ubiquitin with single UBAs at concentrations up to 80 and 40 nM, respectively was observed (FIG. 6E). Interestingly, stoichiometric ratios of TUBE tetra-ubiquitin interactions indicate a mechanism of binding where a single TUBE molecule binds concurrently to more than one tetra-ubiquitin molecule. Furthermore, dissociate on of bound tetra-ubiquitin from the TUBEs appears to exhibit a biphasic behaviour. Fitting a model of parallel decay of two modes of binding to the dissociation phases in FIG. 6 suggests that 10-20% of the bound material dissociates rapidly (koff1≈0.03 s-1; t1/2≈25 s), while the remaining tetra-ubiquitin TUBE complexes display a slower decay, with an estimated half-life of 20-30 minutes (koff2≈4×10-4 s-1). However, experimental data collected over a dissociation period of two hours suggest actual half-lives of the TUBE/tetra-ubiquitin complexes of at least five hours (data not shown). Taking into consideration stoichiometric ratios, the biphasic nature of dissociation and the observed discrepancies in estimated half-lives, a simultaneous occurrence of a variety of binding architectures seems likely.

Figure 6F:
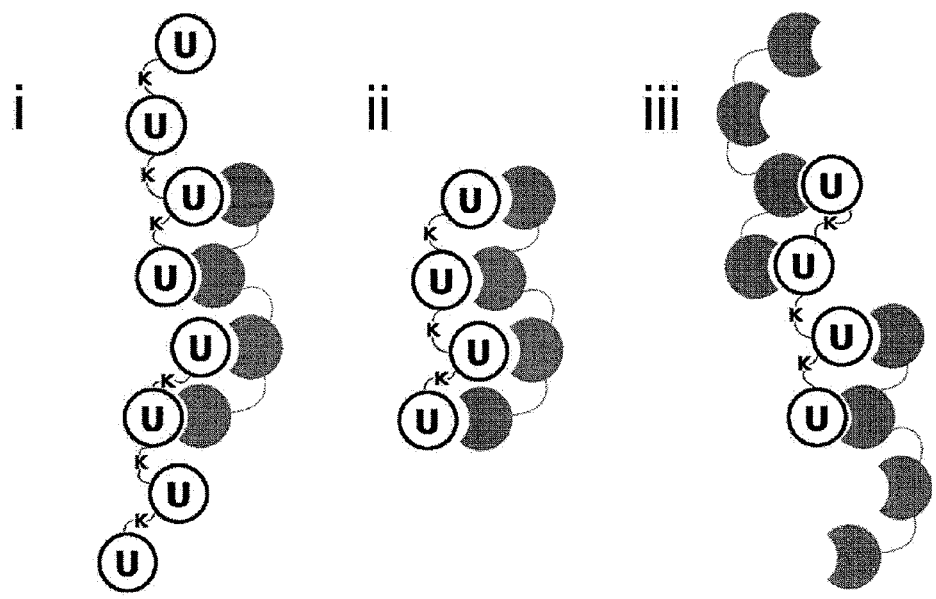

Possibly, weaker tetra-ubiquitin interactions with TUBEs, involving less than four ubiquitin moieties (FIG. 6F(i)), corresponds to a first rapid dissociation, leading to additional TUBE binding site availability for remaining tetra-ubiquitin, which consequently could rearrange, leading to a TUBE interaction involving all of the four ubiquitin units (FIG. 6F(ii) and 6F(iii)), and therefore to a slower decay. Interestingly, at high density TUBE surfaces, and independently of the more marked multiphasic association profiles, similar biphasic dissociation curves as for low density surfaces was observed, indicating that tetra-ubiquitin rebinding during dissociation is mainly due to intramolecular rearrangements (FIG. 6F(ii)).

TABLE II

Equilibrium dissociation constants (Kd) of the interactions K48 or K63 tetra-ubiquitin and TUBEs, compared to those reported for UBAs (*Raasi et al., 2005. Nat Struct Mol Biol, 12, 708-714).

|  | Kd (nM) | Kd(UBA)/Kd(TUBE) |
|---|---|---|
| K63 tetra-ubiquitin | | |
| Ubiquilin1 UBA | 500* | |
| Ubiquilin1 TUBE | 0.60 | 833 |
| hHR23A UBA | 4600* | |
| hHR23A TUBE | 4.88 | 943 |
| K48 tetra-ubiquitin | | |
| Ubiquilin1 UBA | 1200* | |
| Ubiquilin1 TUBE | 14.30 | 84 |
| hHR23A UBA | 6200* | |
| hHR23A TUBE | 9.35 | 663 |

Example 4

TUBEs Efficiently Purify Ubiquitylated Proteins from Cell Extracts

Figure 7A:
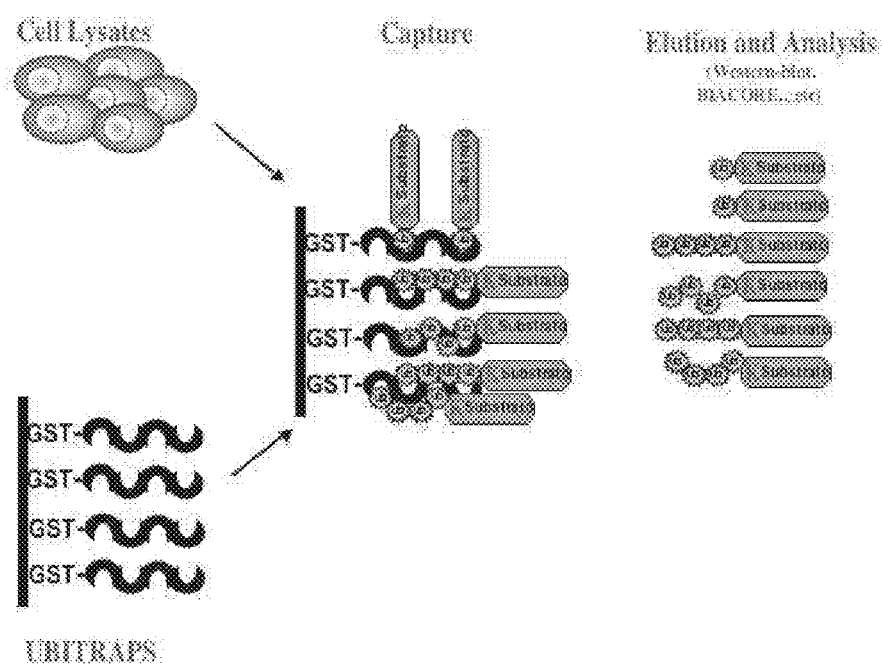
FIGS. 7A through 7D. Capture and analysis of ubiquity-lated proteins from cell extracts.
Figure 7B:
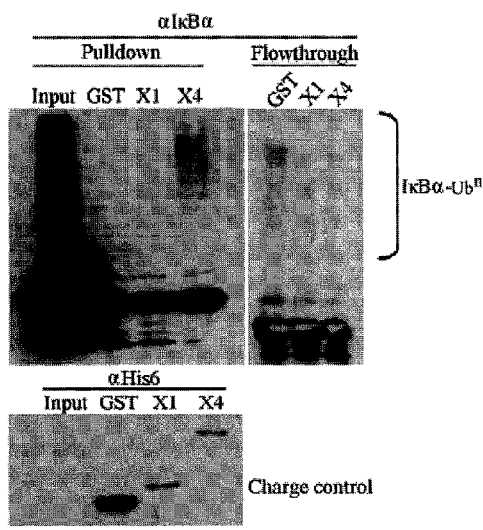
Figure 7C:
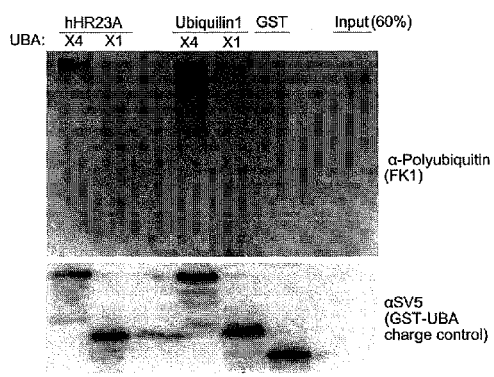
Figure 7D:
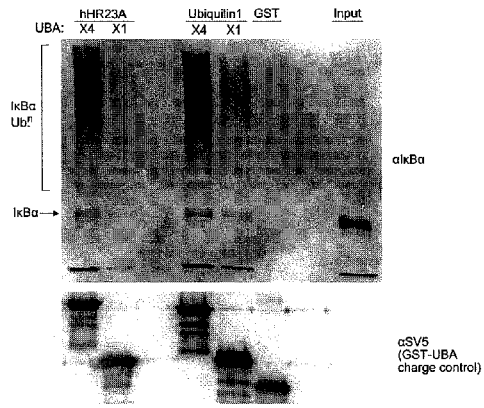
Figure 8A:
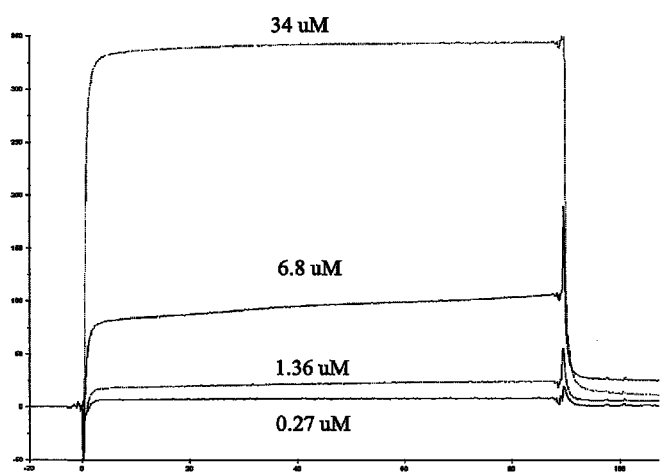
FIGS. 8A and 8B. BiaCore analysis of molecular interactions between K63 tetra ubiquitin covalently attached to CM5 chip surface. Presented sensorgrams have been normalized with respect to analyte molecular weight.
Figure 8B:
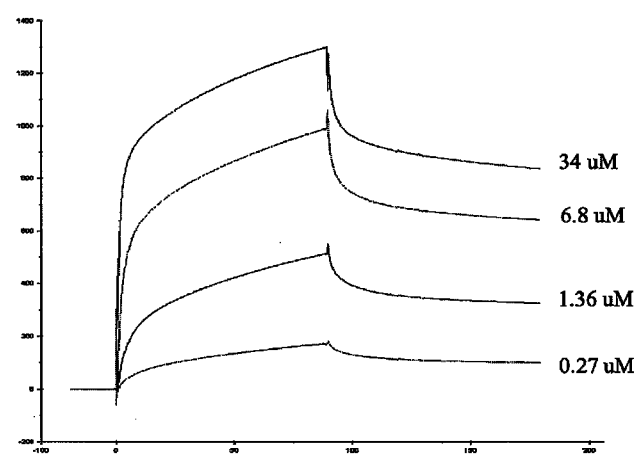

To evaluate the potential use of the polypeptides in the purification of ubiquitylated proteins, cell extracts were prepared and incubated with Sepharose beads bound to different TUBES (FIG. 7A). Washed columns were eluted and bound and unbound fractions analysed by Western blot. For the analysis of ubiquitylated IκBα, cells were incubated during 3 hours with 20 μM of proteasome inhibitors MG132 before 3 hours of stimulation with 20 ng/ml of TNFα, to promote protection and stimulation respectively of ubiquitylated forms of this molecule. The results are shown in FIG. 7B. It was observed that TUBES comprising 4 domains of the UBA domains of hER23A and ubiquilin are capable of retaining polyubiquitylated κBα more efficiently than the corresponding proteins carrying a single ubiquitin binding domain.

To analyse the specificity of the polypeptides as affinity columns, it was decided to analyse their capacity to purify other well-known ubiquitylated proteins such as p53. For these experiments, p53 knock-out cells transiently expressing WTp53 were used as source of ubiquitylated forms of this tumour suppressor. Cells were treated during 3 hours with proteasome inhibitors before lysis and immediate incubation with Sepharose-bound polypeptide comprising the ubiquitin binding domains of p62.

Given the success of the polypeptides as affinity columns, the same constructs were subcloned into pTRE-Tight vector, allowing induction of protein expression upon addition of doxicycline (mediated by the additional pTet-On vector). The aim of this was to increase the efficiency of purification of ubiquitylated proteins from living cells. Tot-p62 polypeptide (Tet on tight-polypeptide comprising ubiquitin binding domains of p62) was co-transfected in epithelial kidney 293 cells and WTp53 expressing cells U2OS. After selection with neomycin, cell populations were pre-treated with proteasome inhibitors and doxocycline before stimulation with TNF or UV irradiation for 293s and U2OS cells respectively. The observations of the inventors suggest that the polypeptides of the invention can be used to purify ubiquitylated proteins from living cells.

Example 5

Comparison of a Conventional Pull Down and a TUBEs Pull Down

Figure 9A:
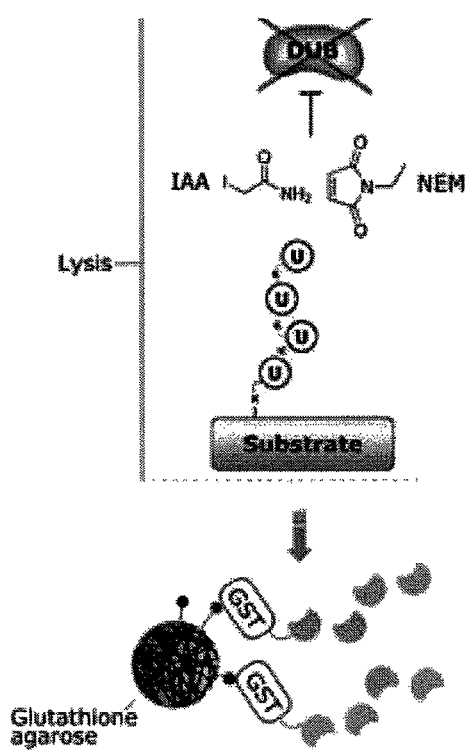
FIGS. 9A through 9D. TUBEs efficiently purify ubiquity-lated proteins from cell extracts.
Figure 9B:
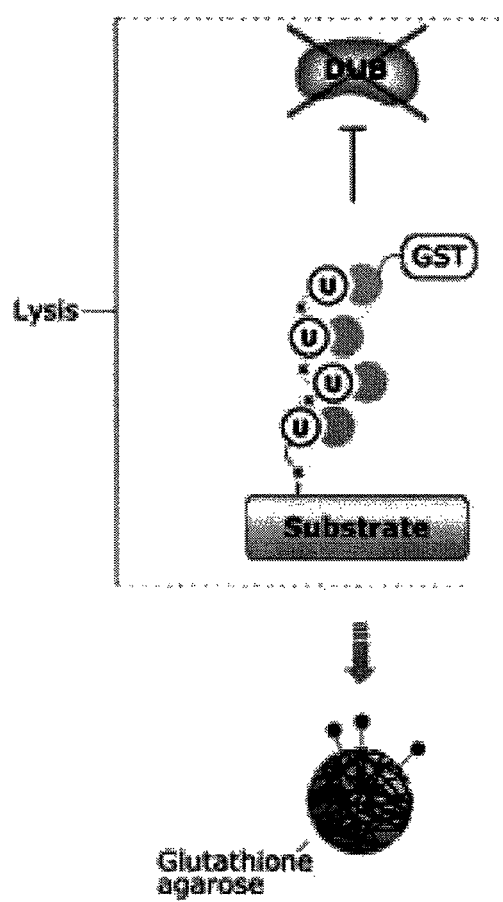
Figure 9C:
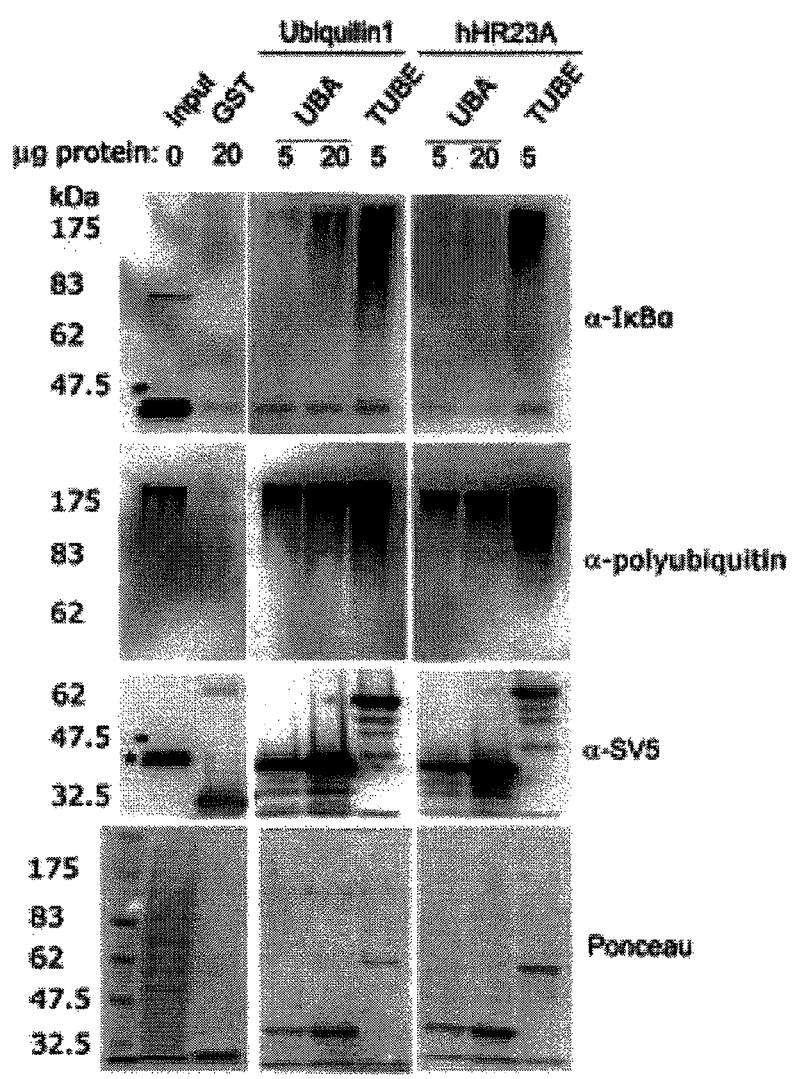
Figure 9D:
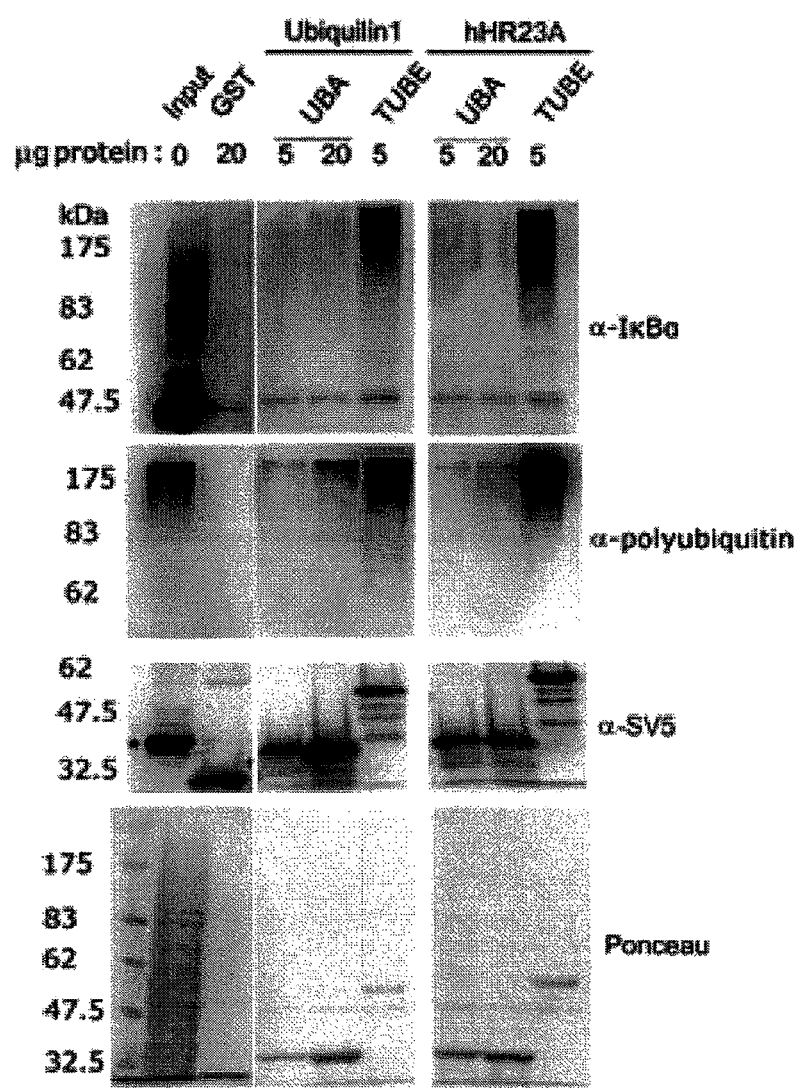

Additionally, to investigate if the TUBEs increased affinity for pure tetra-ubiquitin chains was reflected as improved binding to ubiquitylated proteins, the TUBEs and the single UBA domains were tested for their capacity to pull down IκBα, a protein known to be ubiquitylated upon e.g. TNF-α stimulation, from cell lysates. The total amount of poly-ubiquitylated protein pulled down was detected in parallel. A conventional GST-pull down (FIG. 9A), using IAA/NEM, was compared with a modified method, where lysis was done directly in presence of TUBEs, without IAA/NEM (FIG. 9B). The rationale for this modified method was that the binding of TUBEs to tetra-ubiquitin may be tight enough to allow TUBE-poly-ubiquitin complexes to persist during lysis, and consequently preserve intact complexes during the pull-down process. In both methods, a point of control using four times more GST-fused single UBA domain (six-fold molar excess) was included to investigate if the pulldown efficiency was determined rather by the 'local' or the 'global' UBA domain concentration. In every case, we observed that TUBEs pulled down far more ubiquitylated IκBα and poly-ubiquitylated proteins than single UBA domains (FIG. 9C, FIG. 9D).

Furthermore, while single UBAs were virtually unable to capture any ubiquitylated protein in the modified set-up (FIG. 9D), the drastically increased efficiency of the TUBEs remained equivalent, irrespective of the protocol used. Moreover, a good sample cleanup was achieved with TUBEs, as judged by Ponceau staining (FIG. 9C, FIG. 9D), with minimal loss of specific signal. Taken together, our results show that the increased affinity of TUBEs for tetraubiquitin, relative to that of single UBA domains, was correlated with an improved capacity to capture polyubiquitylated proteins from complex cell lysates. This improvement could not be mimicked by increasing the concentration of single UBA domains, underlining the importance of the tandem arrangement and cooperativity in the superior properties of TUBEs.

Example 6

Figure 10A:
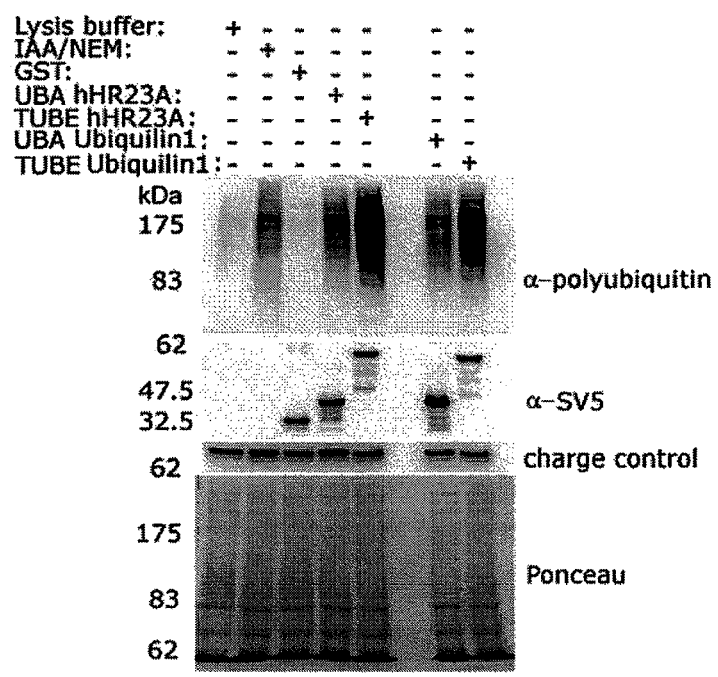
FIGS. 10A through 10F—TUBEs efficiently protect ubiquitylated proteins from de-ubiquitylation and proteasomal degradation.
Figure 10B:
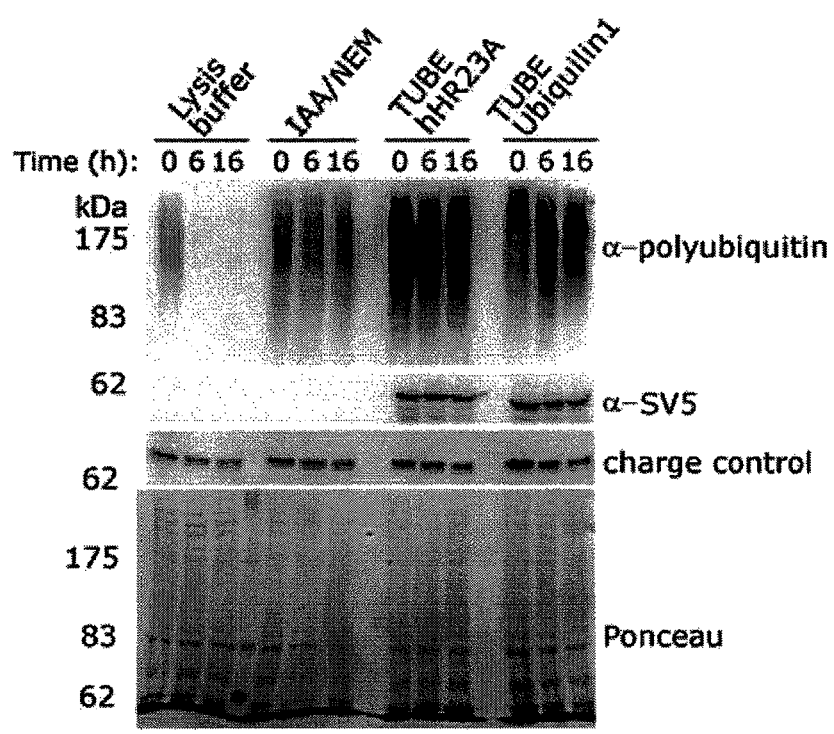
Figure 10C:
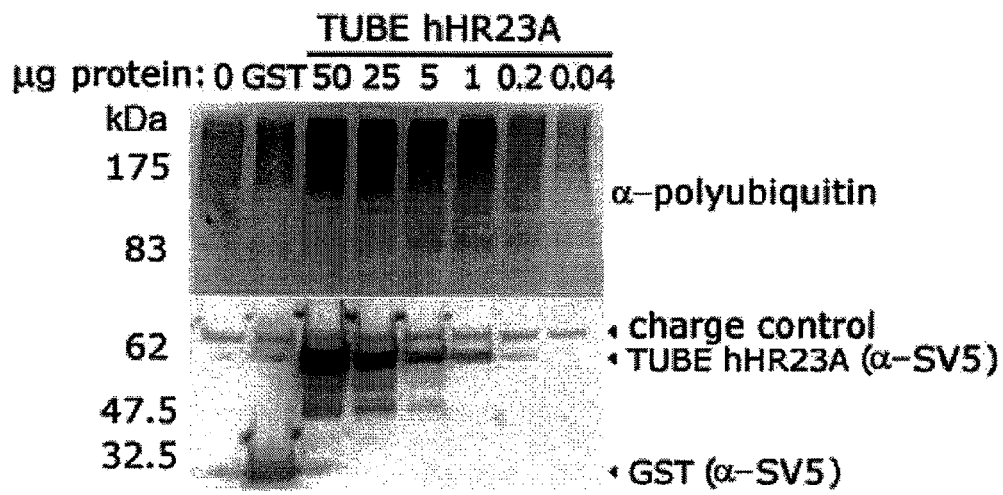
Figure 10D:
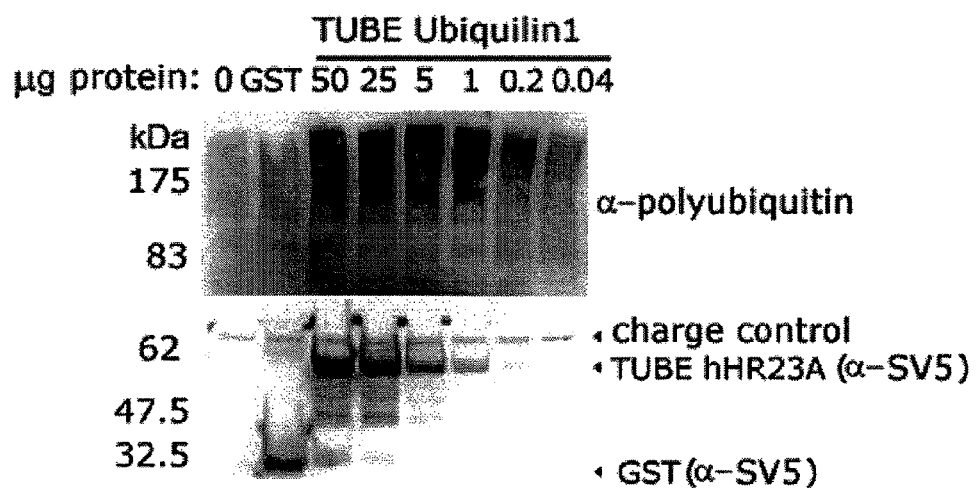

TUBEs Effectively Protect Ubiquitylated Proteins from DUBs and Proteasome Activities To explore if the efficacy of TUBEs could be partly due to an effect of protection from DUBs, cell lysates were incubated for 90 minutes at 25° C. with single UBA domains or with TUBEs (hHR23A or ubiquilin1), and then the amount of polyubiquitylated protein remaining in the supernatants was compared. Lysates treated with IAA/NEM and GST were used as controls. The results show that single UBA domains and IAA/NEM protect proteins from DUBs to similar levels, while TUBEs prevent de-ubiquitylation to a much higher extent (FIG. 10A). Furthermore, TUBEs protective capacity was unaffected after 16 hours of incubation with cell lysates (FIG. 10B) and was detectable even when TUBEs were used at concentrations as low as 0.17 μM (1 μg/100 μl of lysate) (FIG. 10C and FIG. 10D).

Figure 10E:
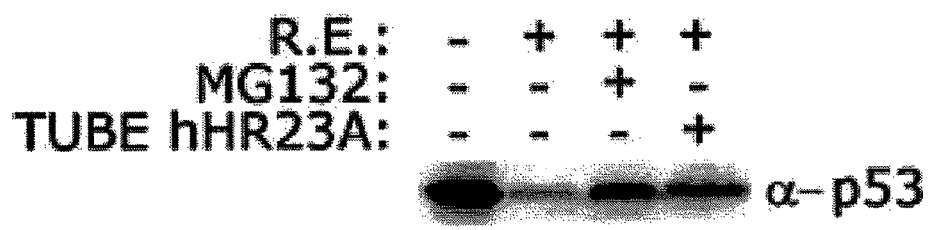
Figure 10F:
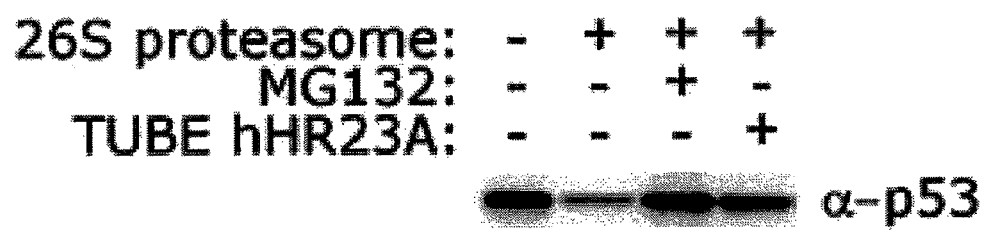

The efficient protection of ubiquitylated proteins observed with the TUBEs might be due to a simultaneous inhibition of DUB action and proteasomal degradation. To address this question, in vitro transcribed-translated p53 was subjected to proteasomal degradation using either reticulocyte extract (RE) or purified proteasomes (PP) (FIGS. 10E and 10F, respectively). It was observed that the degradation of p53 seen upon addition of PP or RE—was blocked by the hHR23A TUBE, at least as efficiently as by the proteasome inhibitor MG132 used at a final concentration of 500 uM. Thus, taken together, these results show that, in cell lysates, TUBEs with a high affinity for tetra-ubiquitin very efficiently protect ubiquitylated proteins from both de-conjugation and proteasomal degradation.

Example 7

TUBEs Quantitatively and Qualitatively Discriminate Stimuli-Mediated Formation of Poly-Ubiquitin Chains on p53 and Mdm2

Figure 11A:
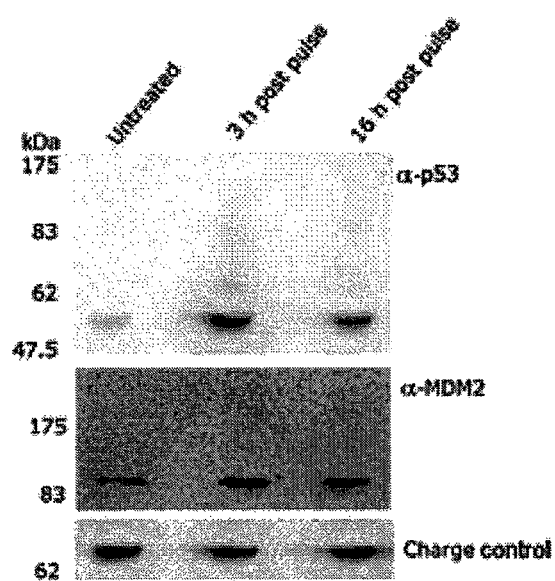
FIGS. 11A through 11C—Detection of endogenous ubiquitylated p53 and MDM2 using TUBEs.
Figure 11B:
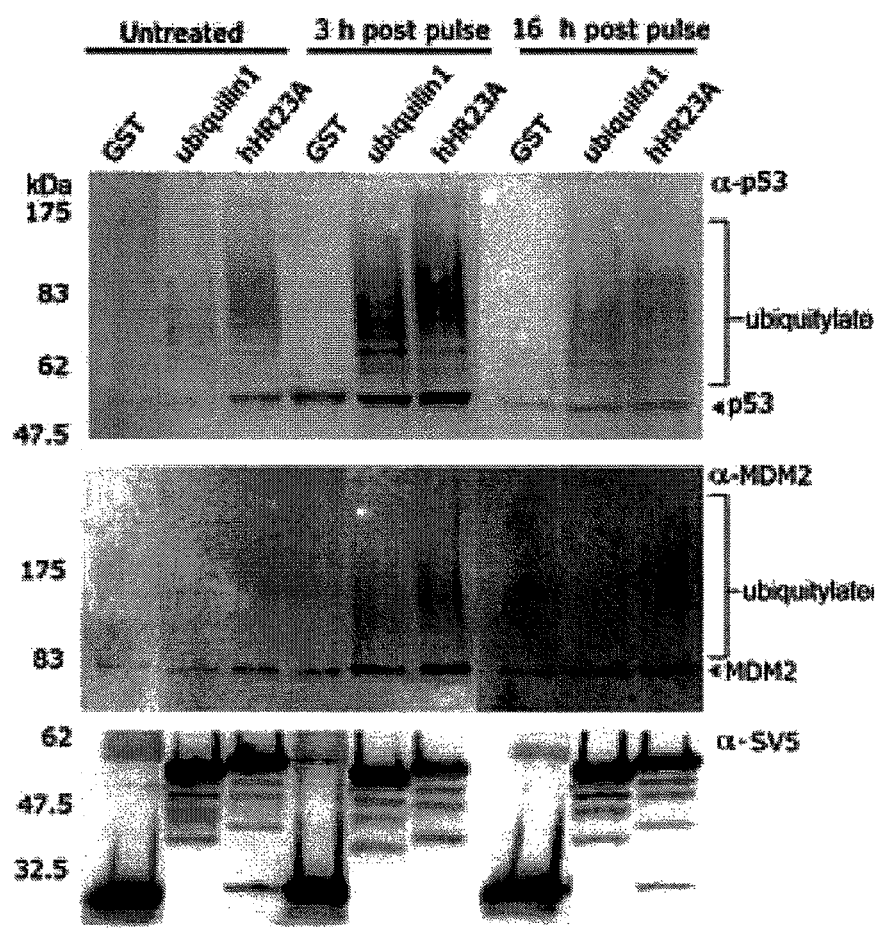

At rest, the p53 tumor suppressor is tightly down-regulated by ubiquitin mediated proteasomal degradation, largely determined by the ubiquitin ligase Mdm2 (Honda, R., et al.,; 1997, FEBS Lett 420, 25-27 and Brooks, C. L. & Gu, W. 2006. Mol Cell 21, 307-315). As a response to genotoxic insult, p53 accumulates and plays its role as inducer of cell cycle arrest or apoptosis (Vogelstein, B., et al,; 2000, Nature 408, 307-310). To determine whether TUBEs could be used to detect oscillations of polyubiquitylated p53 during DNA damage response, Doxorubicin was used in a pulse-chase experiment and the amounts of total p53 and ubiquitylated p53 in MCF7 cells were monitored. Three hours post pulse (10 μM doxorubicin for 1 hour), p53 levels drastically increased, and started to fall down again 16 hours after pulse (FIG. 11A). Using the TUBEs, a pull-down experiment after lysis in the presence of TUBEs was performed (as described above, FIG. 9B). It should be noted that no proteasome (MG132) or DUB (IAA/NEM) inhibitor was used. Both hHR23A and ubiquilin1 TUBEs efficiently purified ubiquitylated p53 (FIG. 11B). Interestingly, using TUBE hHR23A appears to result in pulldown of p53 modified with longer ubiquitin chains, while TUBE ubiquilin1 results in detection of p53 modified with shorter chains. This difference is particularly apparent at three hours post pulse (FIG. 11B). Further, it appears that there is rather a quantitative than qualitative difference in p53 ubiquitylation status, comparing basal with stimulated conditions. MDM2 is itself a substrate for auto-ubiquitylation, which prompted us to probe its state of modification under basal and stressed conditions. Despite poor signal strength due to very low abundance, a significant increase in ubiquitylated MDM2 at three and sixteen hours post pulse, relative to control (FIG. 11B) was observed.

Figure 11C:
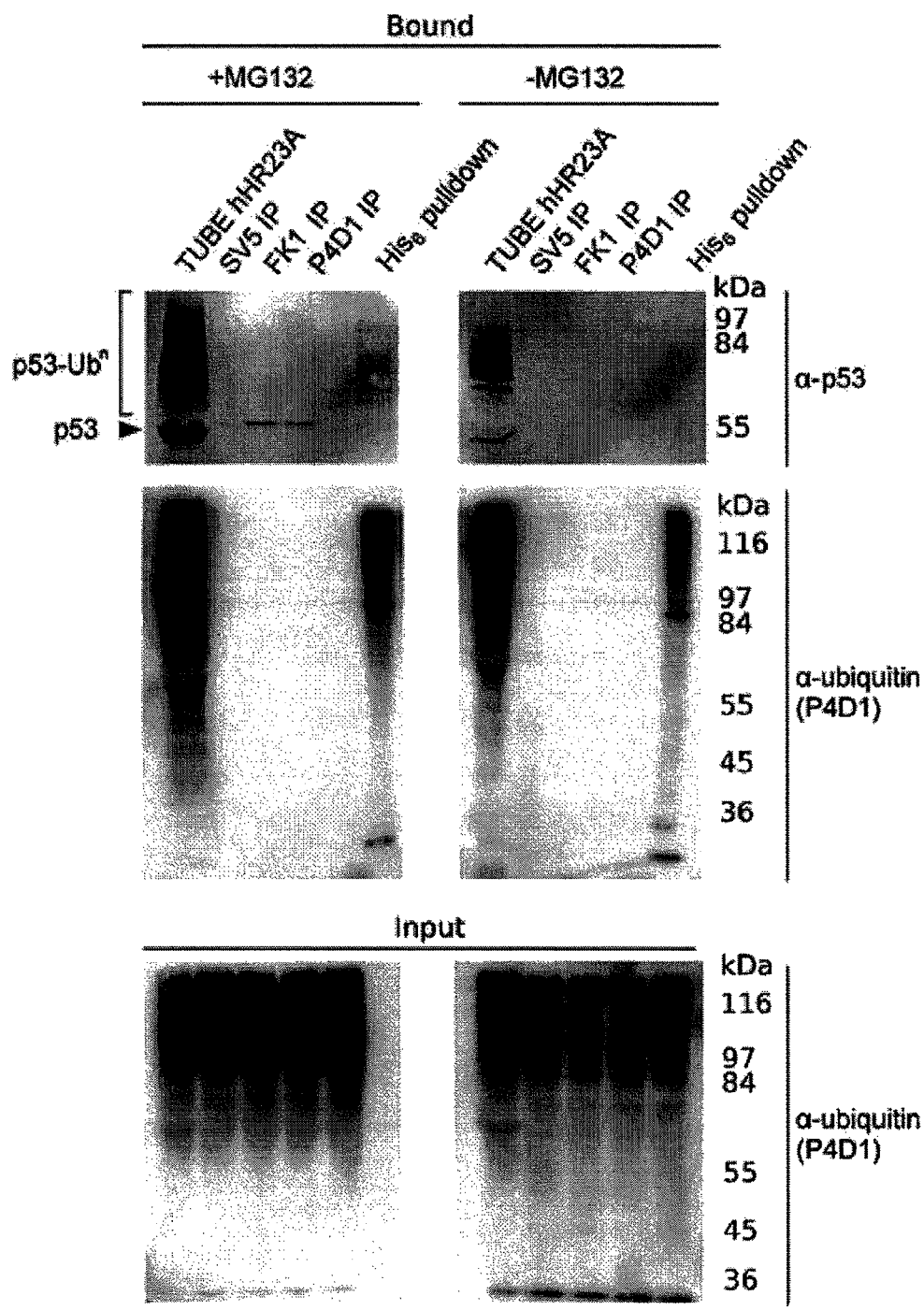

Hence, we show that TUBEs are sensitive enough for the analysis of ubiquitylation of critical endogenous factors during a particular stimulation or cellular event. The efficiency of purification of ubiquitylated p53 using TUBES is largely better than with His6-ubiquitin/nickel beads or anti-ubiquitin antibodies, and is further increased when cells are pre-treated with proteasome inhibitors (FIG. 11C).

Thus, taken together, these results show that TUBEs are sensitive tools which can be applied for the analysis of ubiquitylation of endogenous critical cellular factors oscillating during a particular stimulation or cellular event. They can be used to monitor even low abundance proteins such as Mdm2 and do not require any addition of proteasome or DUB inhibitors.

In nature, several proteins contain more than one ubiquitin or UbL binding domain (Berke et al., 2005 Biol Chem, 280, 32026-32034.), (Tatham et al., 2008 Nat Cell Biol, 10, 538-546.) arguing in favour of an evolutionary functional advantage of increased avidity for polyubiquitylated proteins. Here we demonstrate that this property can be exploited to protect and purify endogenous ubiquitylated proteins from cell extracts in native conditions, without using overexpression methods, which could perturb molecular machineries leading to the formation of irrelevant ubiquitin chains. TUBEs might therefore be an instrumental proteomic tool for the reliable characterization of the ubiquitome by mass spectrometry, contributing to a better understanding of multiple and synchronous ubiquitylation events that occur during a variety of essential cellular events or allowing for instance to compare the nature and quantity of ubiquitylated proteins isolated from ill and healthy tissues.

Example 8

Ubiquitylated Proteins from Animals Tissues can be Purified with TUBEs

Figure 12:
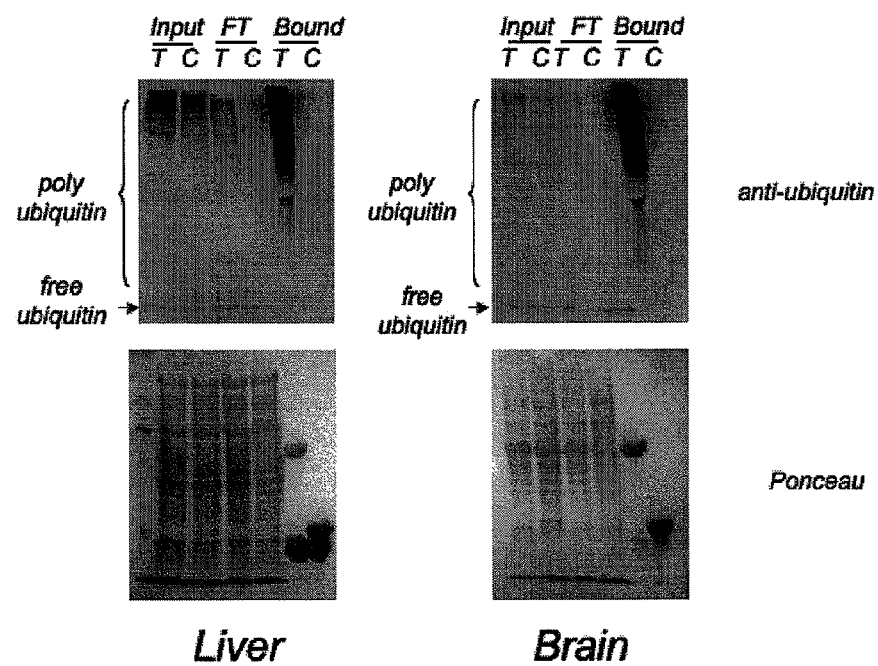
FIG. 12. Purification of ubiquitylated proteins from animal tissues. Proteins where extracted from liver and brain rat tissue and then subjected to pull-down using TUBE immobilized on glutathione agarose beads. Western blot analysis was performed with anti-ubiquitin antibody. The lower panel corresponds to the Ponceau red staining. (T: TUBES, C:Control GST, FT:Flow-through)

Protein extracts from rat liver and brain tissues were prepared. A pulldown with TUBEs was performed on the tissue extracts and the bound and flow-through fractions analyzed by western blotting using anti-ubiquitin antibody. It was observed that TUBES are capable of efficiently retaining polyubiquitylated proteins from tissue extracts (FIG. 12).

CONCLUSIONS

The inventors have developed gene constructs encoding polypeptides comprising at least two ubiquitin binding domains, based on three models of UBA domains. Inventors have engineered up to four repeats of the UBA domains from p62, hHR23A (UBA1) and Ubiquilin1 proteins and fused in a head-to-tail fashion. The UBA domains from p62 have been reported to have preference for K63 linked poly-ubiquitin, while hHR23A (UBA1) have similar affinity for K63 and K48 linked poly-ubiquitin. Finally, the Ubiquilin1 UBA has been reported to have no chain type preference, and in addition interact strongly with mono-ubiquitin. Between each domain, a flexible glycine linker has been included, in order to facilitate proper presentation of the UBA domain. These gene constructs have been constructed to be expressed in bacteria as GST fusion proteins, or in mammalian cells, where their expression can be induced using the doxycycline responsive Tet-On system. Here it is shown that four direct repeats of UBA domains exhibit increased affinity for poly-ubiquitin, and poly-ubiquitylated proteins in vitro, using either GST-polypeptides coupled to glutathione agarose, or BiaCore affinity measurements.

All together the results here show that polypeptides comprising at least two, and more preferably, four UBDs can be efficiently used to analyse ubiquitylated proteins in vitro and ex vivo. The present invention represents an important improvement of the technology described in the prior art for the purification, analysis and detection of ubiquitylated proteins.

The invention claimed is:

1. A polypeptide comprising at least four ubiquitin binding domains, wherein each of said ubiquitin binding domains comprises SEQ ID NO:12 wherein said ubiquitin binding domains are linked to each other via a non-naturally occurring intervening amino acid sequence wherein the non-naturally occurring intervening amino acid sequence is a flexible linker of a sufficient size to allow movement of the ubiquitin binding domains independently of one another maintaining the three-dimensional shape of the individual domain and wherein said flexible linker comprises at least 5 amino acids selected from the group consisting of glycine, serine, alanine and threonine.

2. The polypeptide according to claim 1, wherein said flexible linker is a poly-glycine linker.

3. The polypeptide according to claim 1, wherein said polypeptide further comprises a tag amino acid sequence.

4. The polypeptide according to claim 3, wherein said tag is selected from the group consisting of a detection tag, a purification tag, and combinations thereof.

5. The polypeptide according to claim 4, wherein said detection tag is the Sv5 epitope tag and/or said purification tag is a polyhistidine tag.

6. The polypeptide according to claim 1 wherein said polypeptide is selected from the group consisting of SEQ ID NO: 1.

7. The polypeptide according to claim 1, wherein said polypeptide comprises a GST moiety.

8. The polypeptide of claim 7, wherein said polypeptide is bound to a solid support.

9. The polypeptide according to claim 7, wherein the polypeptide is coupled to a glutathione-modified support.

10. A kit comprising the polypeptide according to claim 1.

11. The kit according to claim 10, further comprising a solid support.

12. The kit according to claim 11, wherein said support is agarose.

13. A polypeptide comprising at least four ubiquitin binding domains, wherein each of said ubiquitin binding domains comprises a polypeptide selected from the group consisting of SEQ ID NO:12, SEQ ID NO:13, SEQ ID NO: 41, SEQ ID NO:15, SEQ ID NO:16 SEQ ID NO:17 and wherein said ubiquitin binding domains are linked to each other via a non-naturally occurring intervening amino acid sequence wherein the non-naturally occurring intervening amino acid sequence is a flexible linker of a sufficient size to allow movement of the ubiquitin binding domains independently of one another maintaining the three-dimensional shape of the individual domain and wherein said flexible linker comprises at least 5 amino acids selected from the group consisting of glycine, serine, alanine and threonine.

14. The polypeptide according to claim 13, wherein said flexible linker is a poly-glycine linker.

15. The polypeptide according to claim 13, wherein said ubiquitin binding domains are the same or different.

16. The polypeptide according to claim 13, wherein said polypeptide is selected from the group consisting of SEQ ID NO:1, SEQ ID NO:2, SEQ ID NO: 3, SEQ ID NO: 4 and SEQ ID NO:5.

17. The polypeptide according to claim 13, wherein said polypeptide further comprises a tag amino acid sequence.

18. The polypeptide according to claim 17, wherein said tag is selected from the group consisting of a detection tag, a purification tag, and combinations thereof.

19. The polypeptide according to claim 18, wherein said detection tag is the Sv5 epitope tag and/or said purification tag is a polyhistidine tag.

20. The polypeptide according to claim 13, wherein said polypeptide comprises a GST moiety.

21. The polypeptide of claim 20, wherein said polypeptide is bound to a solid support.

22. The polypeptide according to claim 21, the polypeptide is coupled to a glutathione-modified support.

23. A kit comprising the polypeptide according to claim 13.

24. The kit according to claim 23, further comprising a solid support.

25. The kit according to claim 24, wherein said support is agarose.

26. A polypeptide comprising at least four ubiquitin binding domains, wherein each of said ubiquitin binding domains comprises a polypeptide selected from the group consisting UBA, UIM, MIU, DIUM, CUE, NZF, A20 ZnF, UBP ZnF, UBZ, UEV, PFU, GLUE, GAT, Jab/MPN, UBM, Ubc, and combinations thereof and wherein said ubiquitin binding domains are linked to each other via a non-naturally occurring intervening amino acid sequence wherein the non-naturally occurring intervening amino acid sequence is a flexible linker of a sufficient size to allow movement of the ubiquitin binding domains independently of one another maintaining the three-dimensional shape of the individual domain and wherein said flexible linker comprises at least 5 amino acids selected from the group consisting of glycine, serine, alanine and threonine.

27. The polypeptide according to claim 26, wherein said flexible linker is a poly-glycine linker.

28. The polypeptide according to claim 26, wherein said ubiquitin binding domains are the same or different.

29. The polypeptide according to claim 26, wherein said polypeptide further comprises a tag amino acid sequence.

30. The polypeptide according to claim 29, wherein said tag is selected from the group consisting of a detection tag, a purification tag, and combinations thereof.

31. The polypeptide according to claim 30, wherein said detection tag is the Sv5 epitope tag and/or said purification tag is a polyhistidine tag.

32. The polypeptide according to claim 26, wherein said polypeptide comprises a GST moiety.

33. The polypeptide of claim 32, wherein said polypeptide is bound to a solid support.

34. A kit comprising the polypeptide according to claim 26.

35. The kit according to claim 34, further comprising a solid support.

36. The kit according to claim 35, wherein said support is agarose.

* * * * *

```
                          SEQUENCE LISTING

<160> NUMBER OF SEQ ID NOS: 41

<210> SEQ ID NO 1
<211> LENGTH: 283
<212> TYPE: PRT
<213> ORGANISM: Homo sapiens

<400> SEQUENCE: 1

His His His His His His Gly Ser Gly Gly Gly Val Thr Gly Ser Glu
1               5                   10                  15

Tyr Glu Thr Met Leu Thr Glu Ile Met Ser Met Gly Tyr Glu Arg Glu
            20                  25                  30

Arg Val Val Ala Ala Leu Arg Ala Ser Tyr Asn Asn Pro His Arg Ala
        35                  40                  45

Val Glu Tyr Leu Leu Thr Gly Ile Pro Gly Ser Pro Glu Pro Glu His
    50                  55                  60

Gly Ser Gly Gly Gly Gly Ser Gly Gly Gly Val Thr Gly Ser Glu Tyr
65                  70                  75                  80

Glu Thr Met Leu Thr Glu Ile Met Ser Met Gly Tyr Glu Arg Glu Arg
                85                  90                  95

Val Val Ala Ala Leu Arg Ala Ser Tyr Asn Asn Pro His Arg Ala Val
            100                 105                 110

Glu Tyr Leu Leu Thr Gly Ile Pro Gly Ser Pro Glu Pro Glu His Gly
        115                 120                 125

Ser Gly Gly Gly Gly Ser Gly Gly Gly Val Thr Gly Ser Glu Tyr Glu
    130                 135                 140

Thr Met Leu Thr Glu Ile Met Ser Met Gly Tyr Glu Arg Glu Arg Val
145                 150                 155                 160

Val Ala Ala Leu Arg Ala Ser Tyr Asn Asn Pro His Arg Ala Val Glu
                165                 170                 175

Tyr Leu Leu Thr Gly Ile Pro Gly Ser Pro Glu Pro Glu His Gly Ser
            180                 185                 190

Gly Gly Gly Gly Ser Gly Gly Gly Val Thr Gly Ser Glu Tyr Glu Thr
        195                 200                 205

Met Leu Thr Glu Ile Met Ser Met Gly Tyr Glu Arg Glu Arg Val Val
    210                 215                 220

Ala Ala Leu Arg Ala Ser Tyr Asn Asn Pro His Arg Ala Val Glu Tyr
225                 230                 235                 240
```

```
Leu Leu Thr Gly Ile Pro Ser Pro Glu Pro His Gly Ser Gly
            245                 250                 255

Gly Gly Gly Ser Pro Glu Phe Pro Gly Val Asp Leu Glu Gly Lys Pro
            260                 265                 270

Ile Pro Asn Pro Leu Leu Gly Leu Glu Ser Thr
            275                 280

<210> SEQ ID NO 2
<211> LENGTH: 263
<212> TYPE: PRT
<213> ORGANISM: Homo sapiens

<400> SEQUENCE: 2

His His His His His His Gly Ser Gly Gly Gly Tyr Ile Gln Val Thr
1               5                   10                  15

Pro Gln Glu Lys Glu Ala Ile Glu Arg Leu Lys Ala Leu Gly Phe Pro
            20                  25                  30

Glu Ser Leu Val Ile Gln Ala Tyr Phe Ala Cys Glu Lys Asn Glu Asn
        35                  40                  45

Leu Ala Ala Asn Phe Leu Leu Ser Gln Asn Phe Asp Asp Gly Gly Gly
    50                  55                  60

Gly Ser Gly Gly Gly Tyr Ile Gln Val Thr Pro Gln Glu Lys Glu Ala
65                  70                  75                  80

Ile Glu Arg Leu Lys Ala Leu Gly Phe Pro Glu Ser Leu Val Ile Gln
                85                  90                  95

Ala Tyr Phe Ala Cys Glu Lys Asn Glu Asn Leu Ala Ala Asn Phe Leu
            100                 105                 110

Leu Ser Gln Asn Phe Asp Asp Gly Gly Gly Gly Ser Gly Gly Gly Tyr
        115                 120                 125

Ile Gln Val Thr Pro Gln Glu Lys Glu Ala Ile Glu Arg Leu Lys Ala
    130                 135                 140

Leu Gly Phe Pro Glu Ser Leu Val Ile Gln Ala Tyr Phe Ala Cys Glu
145                 150                 155                 160

Lys Asn Glu Asn Leu Ala Ala Asn Phe Leu Leu Ser Gln Asn Phe Asp
                165                 170                 175

Asp Gly Gly Gly Gly Ser Gly Gly Gly Tyr Ile Gln Val Thr Pro Gln
            180                 185                 190

Glu Lys Glu Ala Ile Glu Arg Leu Lys Ala Leu Gly Phe Pro Glu Ser
        195                 200                 205

Leu Val Ile Gln Ala Tyr Phe Ala Cys Glu Lys Asn Glu Asn Leu Ala
    210                 215                 220

Ala Asn Phe Leu Leu Ser Gln Asn Phe Asp Asp Gly Gly Gly Gly Ser
225                 230                 235                 240

Pro Glu Phe Pro Gly Val Asp Leu Glu Gly Lys Pro Ile Pro Asn Pro
                245                 250                 255

Leu Leu Gly Leu Glu Ser Thr
            260

<210> SEQ ID NO 3
<211> LENGTH: 247
<212> TYPE: PRT
<213> ORGANISM: Homo sapiens

<400> SEQUENCE: 3

His His His His His His Gly Ser Pro Glu Phe Pro Gly Val Glu Gly
1               5                   10                  15

Gly Gly Pro Arg Leu Ile Glu Ser Leu Ser Gln Met Leu Ser Met Gly
```

-continued

```
                20                  25                  30
Phe Ser Asp Glu Gly Gly Trp Leu Thr Arg Leu Leu Gln Thr Lys Asn
            35                  40                  45

Tyr Asp Ile Gly Ala Ala Leu Asp Thr Ile Gln Tyr Ser Lys His Pro
        50                  55                  60

Gly Gly Gly Val Glu Gly Gly Pro Arg Leu Ile Glu Ser Leu Ser
 65                  70                  75                  80

Gln Met Leu Ser Met Gly Phe Ser Asp Glu Gly Gly Trp Leu Thr Arg
                85                  90                  95

Leu Leu Gln Thr Lys Asn Tyr Asp Ile Gly Ala Ala Leu Asp Thr Ile
            100                 105                 110

Gln Tyr Ser Lys His Pro Gly Gly Gly Val Glu Gly Gly Pro Arg
        115                 120                 125

Leu Ile Glu Ser Leu Ser Gln Met Leu Ser Met Gly Phe Ser Asp Glu
 130                 135                 140

Gly Gly Trp Leu Thr Arg Leu Leu Gln Thr Lys Asn Tyr Asp Ile Gly
145                 150                 155                 160

Ala Ala Leu Asp Thr Ile Gln Tyr Ser Lys His Pro Gly Gly Gly Val
                165                 170                 175

Glu Gly Gly Pro Arg Leu Ile Glu Ser Leu Ser Gln Met Leu Ser
            180                 185                 190

Met Gly Phe Ser Asp Glu Gly Gly Trp Leu Thr Arg Leu Leu Gln Thr
        195                 200                 205

Lys Asn Tyr Asp Ile Gly Ala Ala Leu Asp Thr Ile Gln Tyr Ser Lys
        210                 215                 220

His Pro Gly Gly Gly Val Asp Leu Glu Gly Lys Pro Ile Pro Asn Pro
225                 230                 235                 240

Leu Leu Gly Leu Glu Ser Thr
                245

<210> SEQ ID NO 4
<211> LENGTH: 279
<212> TYPE: PRT
<213> ORGANISM: Homo sapiens

<400> SEQUENCE: 4

His His His His His His Gly Ser Gly Gly Val Asn Pro Gln Leu
 1               5                  10                  15

Gln Asn Pro Glu Val Arg Phe Gln Gln Gln Leu Glu Gln Leu Ser Ala
            20                  25                  30

Met Gly Phe Leu Asn Arg Glu Ala Asn Leu Gln Ala Leu Ile Ala Thr
        35                  40                  45

Gly Gly Asp Ile Asn Ala Ala Ile Glu Arg Leu Leu Gly Ser Gln Pro
    50                  55                  60

Ser Gly Gly Gly Ser Gly Gly Gly Val Asn Pro Gln Leu Gln Asn
 65                  70                  75                  80

Pro Glu Val Arg Phe Gln Gln Gln Leu Glu Gln Leu Ser Ala Met Gly
                85                  90                  95

Phe Leu Asn Arg Glu Ala Asn Leu Gln Ala Leu Ile Ala Thr Gly Gly
            100                 105                 110

Asp Ile Asn Ala Ala Ile Glu Arg Leu Leu Gly Ser Gln Pro Ser Gly
        115                 120                 125

Gly Gly Ser Gly Gly Gly Val Asn Pro Gln Leu Gln Asn Pro Glu
        130                 135                 140

Val Arg Phe Gln Gln Gln Leu Glu Gln Leu Ser Ala Met Gly Phe Leu
```

```
            145                 150                 155                 160
Asn Arg Glu Ala Asn Leu Gln Ala Leu Ile Ala Thr Gly Gly Asp Ile
                165                 170                 175

Asn Ala Ala Ile Glu Arg Leu Leu Gly Ser Gln Pro Ser Gly Gly Gly
            180                 185                 190

Gly Ser Gly Gly Gly Val Asn Pro Gln Leu Gln Asn Pro Glu Val Arg
        195                 200                 205

Phe Gln Gln Gln Leu Glu Gln Leu Ser Ala Met Gly Phe Leu Asn Arg
    210                 215                 220

Glu Ala Asn Leu Gln Ala Leu Ile Ala Thr Gly Gly Asp Ile Asn Ala
225                 230                 235                 240

Ala Ile Glu Arg Leu Leu Gly Ser Gln Pro Ser Gly Gly Gly Gly Ser
                245                 250                 255

Pro Glu Phe Pro Gly Val Asp Leu Glu Gly Lys Pro Ile Pro Asn Pro
            260                 265                 270

Leu Leu Gly Leu Glu Ser Thr
        275

<210> SEQ ID NO 5
<211> LENGTH: 416
<212> TYPE: PRT
<213> ORGANISM: Homo sapiens

<400> SEQUENCE: 5

His His His His His His Gly Ser Pro Glu Phe Pro Gly Val Glu Gly
1               5                   10                  15

Val Asp Pro Ser Ala Asp Pro Glu Leu Ala Leu Ala Leu Arg Val Ser
            20                  25                  30

Met Glu Glu Gln Arg Gln Arg Gln Glu Glu Ala Arg Arg Ala Ala
        35                  40                  45

Ala Ala Ser Ala Ala Glu Ala Gly Ile Ala Thr Thr Gly Thr Glu Asp
    50                  55                  60

Ser Asp Asp Ala Leu Leu Lys Met Ala Ile Ser Gln Gln Glu Phe Gly
65                  70                  75                  80

Arg Thr Gly Leu Pro Asp Leu Ser Ser Met Thr Glu Glu Glu Gln Ile
                85                  90                  95

Ala Tyr Ala Met Gln Met Ser Leu Gln Gly Ala Glu Phe Val Glu Gly
            100                 105                 110

Val Asp Pro Ser Ala Asp Pro Glu Leu Ala Leu Ala Leu Arg Val Ser
        115                 120                 125

Met Glu Glu Gln Arg Gln Arg Gln Glu Glu Ala Arg Arg Ala Ala
    130                 135                 140

Ala Ala Ser Ala Ala Glu Ala Gly Ile Ala Thr Thr Gly Thr Glu Asp
145                 150                 155                 160

Ser Asp Asp Ala Leu Leu Lys Met Ala Ile Ser Gln Gln Glu Phe Gly
                165                 170                 175

Arg Thr Gly Leu Pro Asp Leu Ser Ser Met Thr Glu Glu Glu Gln Ile
            180                 185                 190

Ala Tyr Ala Met Gln Met Ser Leu Gln Gly Ala Glu Phe Val Val Glu
        195                 200                 205

Gly Val Asp Pro Ser Ala Asp Pro Glu Leu Ala Leu Ala Leu Arg Val
    210                 215                 220

Ser Met Glu Glu Gln Arg Gln Arg Gln Glu Glu Ala Arg Arg Ala
225                 230                 235                 240

Ala Ala Ala Ser Ala Ala Glu Ala Gly Ile Ala Thr Thr Gly Thr Glu
```

```
                    245                 250                 255
Asp Ser Asp Asp Ala Leu Leu Lys Met Ala Ile Ser Gln Gln Glu Phe
            260                 265                 270

Gly Arg Thr Gly Leu Pro Asp Leu Ser Ser Met Thr Glu Glu Glu Gln
        275                 280                 285

Ile Ala Tyr Ala Met Gln Met Ser Leu Gln Gly Ala Glu Phe Val Glu
        290                 295                 300

Gly Val Asp Pro Ser Ala Asp Pro Glu Leu Ala Leu Ala Leu Arg Val
305                 310                 315                 320

Ser Met Glu Glu Gln Arg Gln Arg Gln Glu Glu Ala Arg Arg Ala
                325                 330                 335

Ala Ala Ala Ser Ala Ala Glu Ala Gly Ile Ala Thr Thr Gly Thr Glu
            340                 345                 350

Asp Ser Asp Asp Ala Leu Leu Lys Met Ala Ile Ser Gln Gln Glu Phe
        355                 360                 365

Gly Arg Thr Gly Leu Pro Asp Leu Ser Ser Met Thr Glu Glu Glu Gln
        370                 375                 380

Ile Ala Tyr Ala Met Gln Met Ser Leu Gln Gly Ala Glu Phe Val Asp
385                 390                 395                 400

Leu Glu Gly Lys Pro Ile Pro Asn Pro Leu Leu Gly Leu Glu Ser Thr
                405                 410                 415
```

<210> SEQ ID NO 6
<211> LENGTH: 849
<212> TYPE: DNA
<213> ORGANISM: Homo sapiens

<400> SEQUENCE: 6

```
catcaccatc accatcacgg atctggtgga ggtgtgacgg gctctgagta tgagacgatg      60
ctgacggaga tcatgtccat gggctatgag cgagagcggg tcgtggccgc cctgagagcc     120
agctacaaca ccccccaccg agccgtggag tatctgctca cgggaattcc tgggagcccc     180
gagccggaac acggttctgg tggaggtgga tctggtggag gtgtgacggg ctctgagtat     240
gagacgatgc tgacggagat catgtccatg ggctatgagc gagagcgggt cgtggccgcc     300
ctgagagcca gctacaacaa ccccccaccga gccgtggagt atctgctcac gggaattcct     360
gggagccccg agccggaaca cggttctggt ggaggtggat ctggtggagg tgtgacgggc     420
tctgagtatg agacgatgct gacggagatc atgtccatgg gctatgagcg agagcgggtc     480
gtggccgccc tgagagccag ctacaacaac ccccaccgag ccgtggagta tctgctcacg     540
ggaattcctg gagccccga gccggaacac ggttctggtg gaggtggatc tggtggaggt     600
gtgacgggct ctgagtatga gacgatgctg acggagatca tgtccatggg ctatgagcga     660
gagcgggtcg tggccgccct gagagccagc tacaacaacc ccaccgagc cgtggagtat     720
ctgctcacgg gaattcctgg gagccccgag ccggaacacg gttctggcgg cggtggatcc     780
ccggaattcc ccggggtcga cctcgaggga aagccaatac ctaatccact acttggacta     840
gaatccaca                                                             849
```

<210> SEQ ID NO 7
<211> LENGTH: 789
<212> TYPE: DNA
<213> ORGANISM: Homo sapiens

<400> SEQUENCE: 7

```
catcaccatc accatcacgg atctggtgga ggttacatcc aggtgacgcc gcaggagaaa      60
```

```
gaagctatag agaggttgaa ggccctgggc ttcccagaga gcctggtcat ccaggcctat      120
ttcgcgtgtg aaaaaaatga gaacttggct gccaacttcc tcctgagtca gactttgat       180 gacggtggag gtggatctgg tggaggttac atccaggtga cgccgcagga gaaagaagct      240
atagagaggt tgaaggccct gggcttccca gagagcctgg tcatccaggc ctatttcgcg      300
tgtgaaaaaa atgagaactt ggctgccaac ttcctcctga gtcagaactt tgatgacggt      360
ggaggtggat ctggtggagg ttacatccag gtgacgccgc aggagaaaga agctatagag      420
aggttgaagg ccctgggctt cccagagagc ctggtcatcc aggcctattt cgcgtgtgaa      480
aaaaatgaga acttggctgc caacttcctc ctgagtcaga actttgatga cggtggaggt      540
ggatctggtg gaggttacat ccaggtgacg ccgcaggaga agaagctat agagaggttg       600 aaggccctgg gctttcccaga gagcctggtc atccaggcct atttcgcgtg tgaaaaaaat    660
gagaacttgg ctgccaactt cctcctgagt cagaactttg atgacggcgg cggtggatcc      720
ccggaattcc ccggggtcga cctcgaggga agccaatac ctaatccact acttggacta      780
gaatccaca                                                              789

<210> SEQ ID NO 8
<211> LENGTH: 741
<212> TYPE: DNA
<213> ORGANISM: Homo sapiens

<400> SEQUENCE: 8
catcaccatc accatcacgg atccccggaa ttccccgggg tcgagggagg aggtccgcgg       60
ctgattgagt ccctctccca gatgctgtcc atgggcttct ctgatgaagg cggctggctc      120
accaggctcc tgcagaccaa gaactatgac atcggagcgg ctctggacac catccagtat      180
tcaaagcatc ccggtggcgg cgtcgaggga ggaggtccgc ggctgattga gtccctctcc      240
cagatgctgt ccatgggctt ctctgatgaa ggcggctggc tcaccaggct cctgcagacc      300
aagaactatg acatcggagc ggctctggac accatccagt attcaaagca tcccggtggc      360
ggcgtcgagg gaggaggtcc gcggctgatt gagtccctct cccagatgct gtccatgggc      420
ttctctgatg aaggcggctg gctcaccagg ctcctgcaga ccaagaacta tgacatcgga      480
gcggctctgg acaccatcca gtattcaaag catcccggtg gcggcgtcga gggaggaggt      540
ccgcggctga ttgagtccct ctcccagatg ctgtccatgg gcttctctga tgaaggcggc      600
tggctcacca ggctcctgca gaccaagaac tatgacatcg gagcggctct ggacaccatc      660
cagtattcaa agcatcccgg tggcggcgtc gacctcgagg gaaagccaat acctaatcca      720
ctacttggac tagaatccac a                                                741

<210> SEQ ID NO 9
<211> LENGTH: 837
<212> TYPE: DNA
<213> ORGANISM: Homo sapiens

<400> SEQUENCE: 9
catcaccatc accatcacgg atctggaggt ggagtaaatc ctcagctaca gaatccagaa       60
gtcagatttc agcaacaact ggaacaactc agtgcaatgg attttttgaa ccgtgaagca      120
aacttgcaag ctctaatagc aacaggagg gatatcaatg cagctattga aaggttactg      180
ggctcccagc catcaggagg tggaggatct ggaggtggag taaatcctca gctacagaat      240
ccagaagtca gatttcagca acaactggaa caactcagtg caatgggatt tttgaaccgt      300 gaagcaaaact tgcaagctct aatagcaaca ggaggtgata tcaatgcagc tattgaaagg      360
```

-continued

```
ttactgggct cccagccatc aggaggtgga ggatctggag gtggagtaaa tcctcagcta      420
cagaatccag aagtcagatt tcagcaacaa ctggaacaac tcagtgcaat gggattttg      480
aaccgtgaag caaacttgca agctctaata gcaacaggag gtgatatcaa tgcagctatt      540
gaaaggttac tgggctccca gccatcagga ggtggaggat ctggaggtgg agtaaatcct      600
cagctacaga atccagaagt cagatttcag caacaactgg aacaactcag tgcaatggga      660
tttttgaacc gtgaagcaaa cttgcaagct ctaatagcaa caggaggtga tatcaatgca      720
gctattgaaa ggttactggg ctcccagcca tcaggaggtg aggatcccc ggaattcccc      780
ggggtcgacc tcgagggaaa gccaatacct aatccactac ttggactaga atccaca       837
```

<210> SEQ ID NO 10
<211> LENGTH: 1248
<212> TYPE: DNA
<213> ORGANISM: Homo sapiens

<400> SEQUENCE: 10

```
catcaccatc accatcacgg atccccggaa ttccccgggg tcgagggagt agatcccagt       60
gctgatcctg agctggcctt ggcccttcgt gtatctatgg aagagcagcg gcagcggcag      120
gaggaggagg cccggcgggc agctgcagct tctgctgctg aggccgggat tgctacgact      180
gggactgaag actcagacga tgcccctgctg aagatggcca tcagccagca agagtttggc      240
cgcactgggc ttcctgacct aagcagtatg actgaggaag agcagattgc ttatgccatg      300
cagatgtccc tgcagggagc agagtttgtc gagggagtag atcccagtgc tgatcctgag      360
ctggccttgg cccttcgtgt atctatggaa gagcagcggc agcggcagga ggaggaggcc      420
cggcgggcag ctgcagcttc tgctgctgag gccgggattg ctacgactgg gactgaagac      480
tcagacgatg cccctgctgaa gatggccatc agccagcaag agtttggccg cactgggctt      540
cctgacctaa gcagtatgac tgaggaagag cagattgctt atgccatgca gatgtccctg      600
cagggagcag agtttgtcgt cgagggagta gatcccagtg ctgatcctga gctggccttg      660
gcccttcgtg tatctatgga agagcagcgg cagcggcagg aggaggaggc ccggcgggca      720
gctgcagctt ctgctgctga ggccgggatt gctacgactg ggactgaaga ctcagacgat      780
gccctgctga gatggccat cagccagcaa gagtttggcc gcactgggct tcctgaccta      840
agcagtatga ctgaggaaga gcagattgct tatgccatgc agatgtccct gcagggagca      900
gagtttgtcg agggagtaga tcccagtgct gatcctgagc tggccttggc ccttcgtgta      960
tctatggaag agcagcggca gcggcaggag gaggaggccc ggcgggcagc tgcagcttct     1020
gctgctgagg ccgggattgc tacgactggg actgaagact cagacgatgc cctgctgaag     1080
atggccatca gccagcaaga gtttggccgc actgggcttc ctgacctaag cagtatgact     1140
gaggaagagc agattgctta tgccatgcag atgtccctgc agggagcaga gtttgtcgac     1200
ctcgagggaa agccaatacc taatccacta cttggactag aatccaca                 1248
```

<210> SEQ ID NO 11
<211> LENGTH: 8
<212> TYPE: PRT
<213> ORGANISM: Artificial Sequence
<220> FEATURE:
<223> OTHER INFORMATION: poly-glycine flexible linker

<400> SEQUENCE: 11

Gly Gly Gly Val Glu Gly Gly Gly
1               5

```
<210> SEQ ID NO 12
<211> LENGTH: 55
<212> TYPE: PRT
<213> ORGANISM: Homo sapiens

<400> SEQUENCE: 12

Val Thr Gly Ser Glu Tyr Glu Thr Met Leu Thr Glu Ile Met Ser Met
1               5                   10                  15

Gly Tyr Glu Arg Glu Arg Val Val Ala Ala Leu Arg Ala Ser Tyr Asn
            20                  25                  30

Asn Pro His Arg Ala Val Glu Tyr Leu Leu Thr Gly Ile Pro Gly Ser
        35                  40                  45

Pro Glu Pro Glu His Gly Ser
    50                  55

<210> SEQ ID NO 13
<211> LENGTH: 50
<212> TYPE: PRT
<213> ORGANISM: Homo sapiens

<400> SEQUENCE: 13

Tyr Ile Gln Val Thr Pro Gln Glu Lys Glu Ala Ile Glu Arg Leu Lys
1               5                   10                  15

Ala Leu Gly Phe Pro Glu Ser Leu Val Ile Gln Ala Tyr Phe Ala Cys
            20                  25                  30

Glu Lys Asn Glu Asn Leu Ala Ala Asn Phe Leu Leu Ser Gln Asn Phe
        35                  40                  45

Asp Asp
    50

<210> SEQ ID NO 14
<211> LENGTH: 54
<212> TYPE: PRT
<213> ORGANISM: Homo sapiens

<400> SEQUENCE: 14

Pro Arg Leu Ile Glu Ser Leu Ser Gln Met Leu Ser Met Gly Phe Ser
1               5                   10                  15

Asp Glu Gly Gly Trp Leu Thr Arg Leu Leu Gln Thr Lys Asn Tyr Asp
            20                  25                  30

Ile Gly Ala Ala Leu Asp Thr Ile Gln Tyr Ser Lys His Pro Gly Gly
        35                  40                  45

Gly Val Glu Gly Gly Gly
    50

<210> SEQ ID NO 15
<211> LENGTH: 54
<212> TYPE: PRT
<213> ORGANISM: Homo sapiens

<400> SEQUENCE: 15

Val Asn Pro Gln Leu Gln Asn Pro Glu Val Arg Phe Gln Gln Gln Leu
1               5                   10                  15

Glu Gln Leu Ser Ala Met Gly Phe Leu Asn Arg Glu Ala Asn Leu Gln
            20                  25                  30

Ala Leu Ile Ala Thr Gly Gly Asp Ile Asn Ala Ala Ile Glu Arg Leu
        35                  40                  45

Leu Gly Ser Gln Pro Ser
    50
```

<210> SEQ ID NO 16
<211> LENGTH: 19
<212> TYPE: PRT
<213> ORGANISM: Homo sapiens

<400> SEQUENCE: 16

Ser Ala Asp Pro Glu Leu Ala Leu Ala Leu Arg Val Ser Met Glu Glu
1               5                   10                  15

Gln Arg Gln

<210> SEQ ID NO 17
<211> LENGTH: 19
<212> TYPE: PRT
<213> ORGANISM: Homo sapiens

<400> SEQUENCE: 17

Thr Glu Glu Glu Gln Ile Ala Tyr Ala Met Gln Met Ser Leu Gln Gly
1               5                   10                  15

Ala Glu Phe

<210> SEQ ID NO 18
<211> LENGTH: 36
<212> TYPE: DNA
<213> ORGANISM: Artificial Sequence
<220> FEATURE:
<223> OTHER INFORMATION: p62 PCR primer 1

<400> SEQUENCE: 18
ccgctcgagg gaggaggtcc gcggctgatt gagtcc                             36

<210> SEQ ID NO 19
<211> LENGTH: 40
<212> TYPE: DNA
<213> ORGANISM: Artificial Sequence
<220> FEATURE:
<223> OTHER INFORMATION: p62 PCR primer 2

<400> SEQUENCE: 19
cgcgtcgacg ccgccaccgg gatgctttga atactggatg                         40

<210> SEQ ID NO 20
<211> LENGTH: 40
<212> TYPE: DNA
<213> ORGANISM: Artificial Sequence
<220> FEATURE:
<223> OTHER INFORMATION: hHR23 UBA1 PCR primer 1

<400> SEQUENCE: 20
cgcgtcgacg ccgccaccgg gatgctttga atactggatg                         40

<210> SEQ ID NO 21
<211> LENGTH: 37
<212> TYPE: DNA
<213> ORGANISM: Artificial Sequence
<220> FEATURE:
<223> OTHER INFORMATION: hHR23 UBA1 primer 2

<400> SEQUENCE: 21
cgcggatccg gtgccgccag aaccgtgttc cggctcg                            37

<210> SEQ ID NO 22
<211> LENGTH: 36
<212> TYPE: DNA
<213> ORGANISM: Artificial Sequence
<220> FEATURE:
<223> OTHER INFORMATION: hHR23A UBA2 PCR primer 1

```
<400> SEQUENCE: 22
ggaagatctg gtggaggtta catccaggtg acgccg                              36

<210> SEQ ID NO 23
<211> LENGTH: 37
<212> TYPE: DNA
<213> ORGANISM: Artificial Sequence
<220> FEATURE:
<223> OTHER INFORMATION: hHR23A UBA2 PCR primer 2

<400> SEQUENCE: 23
cgcggatccg ccgccctcgt catcaaagtt ctgactc                             37

<210> SEQ ID NO 24
<211> LENGTH: 43
<212> TYPE: DNA
<213> ORGANISM: Artificial Sequence
<220> FEATURE:
<223> OTHER INFORMATION: Ubiquilin 1 PCR primer 1

<400> SEQUENCE: 24
ggaagatctg gaggtggagt aaatcctcag ctacagaatc cag                      43

<210> SEQ ID NO 25
<211> LENGTH: 40
<212> TYPE: DNA
<213> ORGANISM: Artificial Sequence
<220> FEATURE:
<223> OTHER INFORMATION: Ubiquilin1 PCR primer 2

<400> SEQUENCE: 25
cgcggatcct ccacctcctg atggctggga gcccagtaac                          40

<210> SEQ ID NO 26
<211> LENGTH: 36
<212> TYPE: DNA
<213> ORGANISM: Artificial Sequence
<220> FEATURE:
<223> OTHER INFORMATION: S5a PCR primer 1

<400> SEQUENCE: 26
ccgctcgagg gaggagatcc cagtgctgat cctgag                              36

<210> SEQ ID NO 27
<211> LENGTH: 34
<212> TYPE: DNA
<213> ORGANISM: Artificial Sequence
<220> FEATURE:
<223> OTHER INFORMATION: S5a PCR primer 2

<400> SEQUENCE: 27
cgcgtcgacg ccgcctgctc cctgcaggga catc                                34

<210> SEQ ID NO 28
<211> LENGTH: 14
<212> TYPE: PRT
<213> ORGANISM: Artificial Sequence
<220> FEATURE:
<223> OTHER INFORMATION: flexible linker/spacer

<400> SEQUENCE: 28

Ser Gly Gly Thr Ser Gly Ser Thr Ser Gly Thr Gly Ser Thr
1               5                   10

<210> SEQ ID NO 29
```

```
<211> LENGTH: 15
<212> TYPE: PRT
<213> ORGANISM: Artificial Sequence
<220> FEATURE:
<223> OTHER INFORMATION: flexible linker/spacer

<400> SEQUENCE: 29

Ala Gly Ser Ser Thr Gly Ser Ser Thr Gly Pro Gly Ser Thr Thr
1               5                   10                  15

<210> SEQ ID NO 30
<211> LENGTH: 7
<212> TYPE: PRT
<213> ORGANISM: Artificial Sequence
<220> FEATURE:
<223> OTHER INFORMATION: flexible linker/spacer

<400> SEQUENCE: 30

Gly Gly Ser Gly Gly Ala Pro
1               5

<210> SEQ ID NO 31
<211> LENGTH: 7
<212> TYPE: PRT
<213> ORGANISM: Artificial Sequence
<220> FEATURE:
<223> OTHER INFORMATION: tetranectin residues 53-56

<400> SEQUENCE: 31

Gly Thr Lys Val His Met Lys
1               5

<210> SEQ ID NO 32
<211> LENGTH: 13
<212> TYPE: PRT
<213> ORGANISM: Artificial Sequence
<220> FEATURE:
<223> OTHER INFORMATION: human fibronectin residues 1992-2102

<400> SEQUENCE: 32

Pro Gly Thr Ser Gly Gln Gln Pro Ser Val Gly Gln Gln
1               5                   10

<210> SEQ ID NO 33
<211> LENGTH: 5
<212> TYPE: PRT
<213> ORGANISM: Artificial Sequence
<220> FEATURE:
<223> OTHER INFORMATION: human fibronectin residues 2038-2042

<400> SEQUENCE: 33

Gly Thr Ser Gly Gln
1               5

<210> SEQ ID NO 34
<211> LENGTH: 10
<212> TYPE: PRT
<213> ORGANISM: Artificial Sequence
<220> FEATURE:
<223> OTHER INFORMATION: linker peptide

<400> SEQUENCE: 34

Pro Lys Pro Ser Thr Pro Pro Gly Ser Ser
1               5                   10

<210> SEQ ID NO 35
<211> LENGTH: 5
<212> TYPE: PRT
```

```
<213> ORGANISM: Artificial Sequence
<220> FEATURE:
<223> OTHER INFORMATION: protease cleavage site

<400> SEQUENCE: 35

Asp Asp Asp Asp Lys
1               5

<210> SEQ ID NO 36
<211> LENGTH: 4
<212> TYPE: PRT
<213> ORGANISM: Artificial Sequence
<220> FEATURE:
<223> OTHER INFORMATION: protease cleavage site

<400> SEQUENCE: 36

Ile Glu Gly Arg
1

<210> SEQ ID NO 37
<211> LENGTH: 4
<212> TYPE: PRT
<213> ORGANISM: Artificial Sequence
<220> FEATURE:
<223> OTHER INFORMATION: protease cleavage site

<400> SEQUENCE: 37

Ile Asp Gly Arg
1

<210> SEQ ID NO 38
<211> LENGTH: 6
<212> TYPE: PRT
<213> ORGANISM: Artificial Sequence
<220> FEATURE:
<223> OTHER INFORMATION: protease cleavage site

<400> SEQUENCE: 38

Leu Val Pro Arg Gly Ser
1               5

<210> SEQ ID NO 39
<211> LENGTH: 7
<212> TYPE: PRT
<213> ORGANISM: Artificial Sequence
<220> FEATURE:
<223> OTHER INFORMATION: protease cleavage site

<400> SEQUENCE: 39

Glu Asn Leu Tyr Phe Gln Gly
1               5

<210> SEQ ID NO 40
<211> LENGTH: 8
<212> TYPE: PRT
<213> ORGANISM: Artificial Sequence
<220> FEATURE:
<223> OTHER INFORMATION: protease cleavage site

<400> SEQUENCE: 40

Leu Glu Val Leu Phe Gln Gly Pro
1               5

<210> SEQ ID NO 41
<211> LENGTH: 46
<212> TYPE: PRT
<213> ORGANISM: Homo sapiens
```

-continued

```
<400> SEQUENCE: 41

Pro Arg Leu Ile Glu Ser Leu Ser Gln Met Leu Ser Met Gly Phe Ser
1               5                   10                  15

Asp Glu Gly Gly Trp Leu Thr Arg Leu Leu Gln Thr Lys Asn Tyr Asp
            20                  25                  30

Ile Gly Ala Ala Leu Asp Thr Ile Gln Tyr Ser Lys His Pro
        35                  40                  45
```